United States Patent
Zhang et al.

(10) Patent No.: US 8,025,406 B2
(45) Date of Patent: Sep. 27, 2011

(54) SYSTEMS AND METHODS FOR PHOTOACOUSTIC OPTHALMOSCOPY

(75) Inventors: Hao F. Zhang, Milwaukee, WI (US); Shuliang Jiao, Alhambra, CA (US)

(73) Assignees: The UWM Research Foundation, Inc., Milwaukee, WI (US); University of Southern California, Los Angeles, CA (US)

( * ) Notice: Subject to any disclaimer, the term of this patent is extended or adjusted under 35 U.S.C. 154(b) by 0 days.

(21) Appl. No.: 12/726,176

(22) Filed: Mar. 17, 2010

(65) Prior Publication Data

US 2010/0245769 A1    Sep. 30, 2010

Related U.S. Application Data

(60) Provisional application No. 61/160,907, filed on Mar. 17, 2009, provisional application No. 61/335,684, filed on Jan. 11, 2010.

(51) Int. Cl.
*A61B 3/00* (2006.01)
*A61B 3/10* (2006.01)

(52) U.S. Cl. ............... 351/219; 351/200; 351/205

(58) Field of Classification Search ............ 351/219, 351/200, 205–206, 221–222, 246
See application file for complete search history.

(56) References Cited

U.S. PATENT DOCUMENTS

| | | | |
|---|---|---|---|
| 4,267,732 A | 5/1981 | Quate | |
| 4,764,005 A * | 8/1988 | Webb et al. | 351/205 |
| 5,062,297 A | 11/1991 | Hashimoto et al. | |
| 5,196,006 A | 3/1993 | Klopotek et al. | |
| 5,521,657 A | 5/1996 | Klopotek | |
| 5,557,352 A | 9/1996 | Nordquist | |
| 5,829,439 A | 11/1998 | Yokosawa et al. | |
| 5,840,023 A | 11/1998 | Oraevsky et al. | |
| 6,309,352 B1 | 10/2001 | Oraevsky et al. | |
| 6,423,001 B1 | 7/2002 | Abreu | |
| 6,652,459 B2 | 11/2003 | Payne et al. | |
| 6,671,043 B1 | 12/2003 | Huettman | |
| 6,849,210 B2 | 2/2005 | Bothe et al. | |
| 6,979,292 B2 | 12/2005 | Kanayama et al. | |
| 7,404,637 B2 | 7/2008 | Miller et al. | |
| 2005/0070803 A1 | 3/2005 | Cullum et al. | |
| 2006/0184042 A1 | 8/2006 | Wang et al. | |

(Continued)

FOREIGN PATENT DOCUMENTS

WO    2007/035934    3/2007

(Continued)

OTHER PUBLICATIONS

A. de la Zerda, et al., "Photoacoustic Ocular Imaging", Optics Letters, vol. 35, No. 3, pp. 270-272, Feb. 1, 2010.

(Continued)

*Primary Examiner* — Dawayne A Pinkney
(74) *Attorney, Agent, or Firm* — Michael Best & Friedrich LLP

(57) ABSTRACT

Various embodiments of the present invention include systems and methods for multimodal functional imaging based upon photoacoustic and laser optical scanning microscopy. In particular, at least one embodiment of the present invention utilizes a contact lens in combination with an ultrasound transducer for purposes of acquiring photoacoustic microscopy data. Traditionally divergent imaging modalities such as confocal scanning laser opthalmoscopy and photoacoustic microscopy are combined within a single laser system. Functional imaging of biological samples can be utilized for various medical and biological purposes.

31 Claims, 10 Drawing Sheets

U.S. PATENT DOCUMENTS

| | | | |
|---|---|---|---|
| 2007/0299341 A1 | 12/2007 | Wang et al. | |
| 2008/0033262 A1 | 2/2008 | Peyman et al. | |
| 2008/0088838 A1 | 4/2008 | Raicu et al. | |
| 2008/0123083 A1 | 5/2008 | Wang et al. | |
| 2010/0245766 A1 | 9/2010 | Zhang et al. | |
| 2010/0245770 A1 | 9/2010 | Zhang et al. | |
| 2010/0249562 A1 | 9/2010 | Zhang et al. | |
| 2010/0268042 A1 | 10/2010 | Wang et al. | |

FOREIGN PATENT DOCUMENTS

| | | |
|---|---|---|
| WO | 2010/107930 | 9/2010 |
| WO | 2010/107933 | 9/2010 |

OTHER PUBLICATIONS

A. de la Zerda, et al., "Photoacoustic Imaging of the Eye for Improved Disease Detection", Presentation No. 0043, Scientific Session 1: Emerging Optical and Optoacoustic Technologies, Sep. 24, 2009.

H.F. Zhang, et al., "Collecting Back-Reflected Photons in Photoacoustic Microscopy", Optics Express, vol. 18, pp. 1278-1282, 2010.

H.F. Zhang, et al., "Functional Photoacoustic Microscopy for High-Resolution and Noninvasive in vivo Imaging," Nature Biotechnology, vol. 24, No. 7, pp. 848-851 Jul. 2006.

H.F. Zhang, et al., "Imaging of Hemoglobin Oxygen Saturation Variations in Single Vessels in vivo Using Photoacoustic Microscopy", Applied Physics Letters 90, 053901, 2007.

H.F. Zhang, et al., "Naturally Combined Photoacoustic Microscopy and Optical Coherence Tomography for Simultaneous Multimodal Imaging", 2009.

Molecular Expressions, Optical Microscopy Primer, Introduction to Optical Imaging, and Photomicrography, available online at: <http://micro.magnet.fsu.edu/primer/index.html>, Jan. 16, 2009.

N.A. Nassif, et al., "In vivo High-Resolution Video-Rate Spectral-Domain Optical Coherence Tomography of the Human Retina and Optic Nerve," Optics Express, vol. 12, No. 3, pp. 367-376, 2004.

L.E.H. Smith, et al., "Oxygen-Induced Retinopathy in the Mouse", Investigative Ophthalmology and Visual Science, vol. 35, No. 1, pp. 101-111, Jan. 1994.

PCT/US2010/027682 International Search Report and Written Opinion dated May 19, 2010 (9 pages).

S. Jiao, et al., "Integrated Photoacoustic Microscopy and Fiber-Optic Confocal Microscopy Using a Signal Laser Source" Proceedings of Asa Biomed, Miami, FL (2010).

S. Jiao, et al., "Photoacoustic Ophthalmoscopy for in vivo Retinal Imaging", Optics Express, vol. 18, 3967-3972, Feb. 15, 2010.

S. Jiao, et al., "Simultaneous Multimodal Imaging with Integrated Photoacoustic Microscopy and Optical Coherence Tomography," Optics Letters, vol. 34, No. 19, pp. 2961-2963, Oct. 1, 2009.

A. de la Zerda, et al., "Carbon Nanotubes as Photoacoustic Molecular Imaging Agents in Living Mice," Nature Nanotechnology, vol. 3, pp. 557-562, Sep. 2008.

A. Harris, et al., "A Review of Methods for Human Retinal Oximetry," Ophthalmic Surgery & Lasers Imaging, vol. 34, No. 2, pp. 152-164, Mar./Apr. 2003.

A. Mendivil, et al., "Ocular Blood Flow Velocities in Patients with Proliferative Diabetic Retinopathy and Healthy Volunteers: A Prospective Study", British Journal of Ophthalmology, vol. 79, pp. 413-416, 1995.

A. Yoshida, et al., "Retinal Blood-Flow Alterations During Progression of Diabetic-Retinopathy", Arch Ophthalmol., vol. 101, pp. 225-227, Feb. 1983.

A.A. Oraevsky, et al., "Optoacoustic Tomography", Biomedical Photonics Handbook, vol. PM125, pp. 1-34 (CRC Press, Boca Raton, FL, 2003).

H.W. van Dijk, et al., "Selective Loss of Inner Retinal Layer Thickness in Type I Diabetic Patients with Minimal Diabetic Retinopathy", Investigative Ophthalmology and Visual Science, vol. 50, No. 7, pp. 3404-3409, Jul. 2009.

A.F. Fercher, et al., "Measurement of Intraocular Distances by Backscattering Spectral Interferometry," Optics Communications, vol. 117, pp. 43-48, May 15, 1995.

A. von Ruckmann, et al., "Distribution of Fundus Autofluorescence with a Scanning Laser Ophthalmoscope", British Journal of Ophthalmology, vol. 79, pp. 407-412, 1995.

B. Khoobehi, et al., "Hyperspectral Imaging for Measurement of Oxygen Saturation in the Optic Nerve Head", Investigative Ophthalmology and Visual Science, vol. 45, No. 5, pp. 1464-1472, May 2004.

B.A. Bower, et al., "Real-Time Spectral Domain Doppler Optical Coherence Tomography and Investigation of Human Retinal Vessel Autoregulation", Journal of Biomedical Optics, vol. 12, No. 4, Jul./Aug. 2007.

B.R. White, et al., "In vivo Dynamic Human Retinal Blood Flow Imaging Using Ultra-High-Speed Spectral Domain Optical Doppler Tomography", Optics Express, vol. 11, No. 25, pp. 3490-3497, Dec. 15, 2003.

C.A. Patil, et al., "Combined Raman Spectroscopy and Optical Coherence Tomography Device for Tissue Characterization", Optics Letters, vol. 33, No. 10, pp. 1135-1137, May 15, 2008.

C.C. Huang, et al., "Determining the Acoustic Properties of the Lens Using a High Frequency Ultrasonic Needle Transducer", Ultrasound in Medicine & Biology, vol. 33, No. 12, pp. 1971-1977, 2007.

C.J. Pavlin, et al., "Ultrasound Biomicroscopy High-Frequency Ultrasound Imaging of the Eye at Microscopic Resolution", Radiologic Clinics of North America, vol. 36, issue 6, pp. 1047-1058, Nov. 1998.

D. Huang, et al., "Optical Coherence Tomography," Science, vol. 254, No. 5035, pp. 1178-1181, Nov. 22, 1991.

G.L. Trick, et al., "Early Supernormal Retinal Oxygenation Response in Patients with Diabetes", Investigative Ophthalmology and Visual Science, vol. 47, No. 4, pp. 1612-1619, Apr. 2006.

G.A. Williams, et al., "Single-Field Fundus Photography for Diabetic Ritinopathy Screening: A Report by the American Academy of Ophthalmology" Ophthalmology, vol. 111, No. 5, pp. 1055-1062, May 2004.

G.E. Lang, "Optical Coherence Tomography Findings in Diabetic Retinopathy", Developments in Ophthalmology, vol. 39, pp. 31-47, 2007.

G.A. A Lutty, et al. Proceedings of the Third International Symposium on Retinopathy of Prematurity: An Update on ROP from the Lab to the Nursery (Nov. 2003, Anaheim, California). Molecular Vision, vol. 12, pp. 532-580, 2006.

G. van Leeuwen, et al., "High-Flow-Velocity and Shear-Rate Imaging by use of Color Doppler Optical Coherence Tomography", Optics Letters, vol. 24, No. 22, pp. 1584-1586, Nov. 15, 1999.

G. Mannino, et al., "Ultrasound Biomicroscopy of the Peripheral Retina and the Ciliary Body in Degenerative Retinoschisis Associated with Pars Plana Systs", British Journal of Ophthalmology, vol. 85, pp. 976-982, 2001.

F.L. Ferris, et al., "Treatment of Diabetic Retinopathy", The New England Journal of Medicine, vol. 341, No. 9, pp. 667-678, Aug. 26, 1999.

F.C. Delori, et al., "Monochromatic Ophthalmoscopy and Fundus Photography," Arch. Ophthalmol, vol. 95, pp. 861-868, May 1977.

F. Ferris, "Early Photocoagulation in Patients with Either Type I or Type II Diabetes", Trans Am Ophthalmol Soc., vol. 94, pp. 505-537, 1996.

D.Y. Yu, et al., "Pathogenesis and Intervention Strategies in Diabetic Retinopathy" Clinical and Experimental Ophthalmology, vol. 29, pp. 164-166, 2001.

E.Z. Zhange, et al., "In vivo High-Resolution 3D Photoacoustic Imaging of Superficial Vascular Anatomy," Physics in Medicine and Biology, vol. 54, pp. 1035-1046, 2009.

B. Ricci, "Oxygen-Induced Retinopathy in the Rat Model", Documenta Ophthalmologica, vol. 74, pp. 171-177, 1990.

C. Biallosterski, et al., "Decreased Optical Coherence Tomography-Measured Pericentral Retinal Thickness in Patients with Diabetics Mellitus Type 1 with Minimal Diabetic Retinopathy", Br. J. Ophthalmol, vol. 91, pp. 1135-1138, 2007.

J. Jiang, et al., "Inhibition of Retinal Neovascularization by Gene Transfer of Small Interfering RNA Targeting HIF-1x and VEGF", Journal of Cellular Physiology, vol. 218, pp. 66-74, 2009.

PCT/US2010/027685 International Search Report and Written Opinion dated May 18, 2010 (9 pages).

H. Wehbe, et al., "Automatic Retinal Blood Flow Calculation Using Spectral Domain Optical Coherence Tomography", Optics Express, vol. 15, No. 23, pp. 15193-15206, Nov. 12, 2007.

H.F. Zhang, et al., "An Automatic Algorithm for Skin Profile Detection in Photoacoustic Microscopy", Journal of Biomedical Optics, vol. 14, No. 2, Mar./Apr. 2009.

H.F. Zhang, et al., "In vivo Imaging of Subcutaneous Structures Using Functional Photoacoustic Microscopy", Nature Protocols vol. 2, No. 4, pp. 797-804, 2007.

H.F. Zhang, et al., "In vivo Volumetric Imaging of Subcutaneous Microvasculature using Photoacoustic Microscopy", Optics Express vol. 14, No. 20, pp. 9317-9323, Oct. 2, 2006.

H.P. Hammes, et al., "Pericytes and the Pathogenesis of Diabetic Retinopathy", Diabetes, vol. 51, pp. 3107-3112, Oct. 2002.

H. Ren, et al., "Imaging and Quantifying Transverse Flow Velocity with the Doppler Bandwidth in a Phase-Resolved Functional Optical Coherence Tomography", Optics Letters vol. 27, No. 6, pp. 409-411, Mar. 15, 2002.

J. Cai, et al., "The Pathogenesis of Diabetic Retinopathy: Old Concepts and New Questions," Eye, vol. 16, pp. 242-260, 2002.

M. Ushio-Fukai, et al., "Reactive Species and Angiogenesis: NADPH Oxidase as Target for Cancer Therapy", Cancer Lett., vol. 266, No. 1, pp. 37-52, Jul. 18, 2008.

J. Laufer, et al., "Three-Dimensional Noninvasive Imaging of the Vasculature in the Mouse Brain Using a High Resolution Photoacoustic Scanner," Applied Optics, vol. 48, No. 10, pp. D299-D306, Apr. 1, 2009.

J.A. Olson, et al., "A Comparative Evaluation of Digital Imaging, Retinal Photography and Optometrist Examination in Screening for Diabetic Retinopathy", Diabetic Medicine, vol. 20, pp. 528-534, accepted Aug. 20, 2002.

J.G. Cunha-Vaz, "Diabetic Retinopathy: Surrogate Outcomes for Durg Development for Diabetic Retinopathy", Ophthalmologica, vol. 214, pp. 377-380, 2000.

J.H. Kempen, et al., "The Prevalence of Diabetic Retinopathy Among Adults in the United States", Arch Ophthalmol., vol. 122, pp. 552-563, Apr. 2004.

J.R. MacKinnon, et al., "Colour Doppler Imaging of the Ocular Circulation in Diabetic Retinopathy", Acta Ophthalmologica Scandinavica, vol. 78, pp. 386-389, 2000.

J.S. Penn, et al "Exposure to Alternating Hypoxia Causes Severe Proliferative Retinopathy in the Newborn Rat", Pediatric Research, vol. 36, No. 6, pp. 724-731, 1994.

J.S. Penn, et al "Fluorescein Angiography as a Means of Assessing Retinal Vascular Pathology in Oxygen-Exposed Newborn Rats", Current Eye Research, vol. 12, No. 6, pp. 561-570, 1993.

J.S. Penn, et al., "The Range of PaO2 Variation Determines the Severity of Oxygen-Induced Retinopathy in Newborn Rats", Investigative Ophthalmology and Visual Science, vol. 36, No. 10, pp. 2063-2070, Sep. 1995.

K. Guan, et al., "Retinal Hemodynamics in Early Diabetic Macular Edema", Diabetes, vol. 55, pp. 813-818, Mar. 2006.

K. Maslov, et al., "Effects of Wavelength-Dependent Fluence Attenuation on the Noninvasive Photoacoustic Imaging of Hemoglobin Oxygen Saturation in Subcutaneous Vasculature in vivo", Inverse Problems, vol. 23, pp. S113-S122, 2007.

K. Maslov, et al., "Optical-Resolution Photoacoustic Microscopy for in vivo Imaging of Single Capillaries," Optics Letters, vol. 33, No. 9, pp. 929-931, May 1, 2008.

K.H. Song, et al., "Near-Infrared Gold Nanocages as a New Class of Tracers for Photoacoustic Sentinel Lymph Node Mapping on a Rat Model," Nano Letters, vol. 9, No. 1, pp. 183-188, 2009.

K.K. Shung, et al., "Piezoelectric Materials for High Frequency Medical Imaging Applications: A Review", Journal of Electronic Ceramic, vol. 19, pp. 139-145, 2007.

K.R. Denninghoff, et al., "Retinal Imaging Techniques in Diabetes", Diabetes Technology & Therapeutics, vol. 2, No. 1, pp. 111-113, 2000.

L.P. Aiello, "Angiogenic Pathways in Diabetic Retinopathy", New England Journal of Medicine, vol. 353, No. 8, pp. 839-841, Aug. 25, 2005.

L.V. Wang, "Multiscale Photoacoustic Microscopy and Computed Tomography," Nature Photonics, vol. 3, pp. 503-509, Sep. 2009.

L.V. Wang, "Tutorial on Photoacoustic Microscopy and Computed Tomography", IEEE Journal of Selected Topics in Quantum Electronics vol. 14, No. 1, pp. 171-179, Jan./Feb. 2008.

M. Hammer, et al., "Light Paths in Retinal Oximetry," IEEE Transactions on Biomedical Engineering, vol. 48, No. 5, pp. 592-598, May 2001.

M. Lorenzi, et al., "Retinal Haemodynamics in Individuals with Well-Controlled Type 1 Diabetes", Diabetologia, vol. 51, pp. 361-364, 2008.

M. Ruggeri, et al., "In vivo Three-Dimensional High-Resolution Imaging of Rodent Retina with Spectral-Domain Optical Coherence Tomography," Investigative Ophthalmology & Visual Science, vol. 48, No. 4, pp. 1808-1814, Apr. 2007.

M. Ruggeri, et al., "Quantitative Evaluation of Retinal Tumor Volume in Mouse Model of Retinoblastoma by Using Ultra High-Resolution Optical Coherence Tomography", Journal of Innovation in Optical Health Science, vol. 1, No. 1, pp. 1-12, 2008.

M. Sivaramakrishnan, et al., "Limitations of Quantitative Photoacoustic Measurement of Blood Oxygenation in Small Vessels", Physics in Medicine and Biology, vol. 52, pp. 1349-1361, 2007.

M. Wojtkowski, et al., "In vivo Human Retinal Imaging by Fourier Domain Optical Coherence Tomography," Journal of Biomedical Optics, vol. 7, No. 3, pp. 457-463, Jul. 2002.

O. Strauss, "The Retinal Pigment Epithelium in Visual Function," Physiol. Rev., vol. 85, pp. 845-881, Jul. 2005.

P. Geisen, et al., "Neutralizing Antibody to VEGF Reduces Intravitreous Neovascularization and may Not Interfere with Ongoing Intraretinal Vascularization in a Rat Model of Retinopathy of Prematurity", Molecular Vision, vol. 14, pp. 354-357, 2008.

P. Pechan, et al., "Novel Anti-VEGF Chimeric Molecules Delivered by AAV Vectors for Inhibition of Retinal Neovascularization", Gene Therapy, vol. 16, pp. 10-16, 2009.

P. Sharp, et al., "The Scanning Laser Ophthalmoscope—A Review of its Role in Bioscience and Medicine", Physics in Medicines and Biology, vol. 49, pp. 1085-1096, 2004.

Q. Zhou, et al., "Design and Fabrication of PZN-7%PT Single Crystal High Frequency Angled Needle Ultrasound Transducers", IEEE Transactions on Ultrasonics, Ferroelectrics, and Frequency Control, vol. 55, No. 6, pp. 1394-1399, 2008.

Q.F. Zhou, et al., "PMN-PT Single Crystal High Frequency Ultrasonic Needle Transducers for Pulsed Wave Doppler Application", IEEE Transactions on Ultrasonics, Ferroelectrics, and Frequency Control, vol. 54, No. 3, pp. 668-675, Mar. 2007.

R. Zemp, et al., "Stochastic Explanation of Speckle Contrast Detection in Ultrasound-Modulated Optical Tomography", Physical Review, E 73, 2006.

R.G.M. Kolkman, et al., "In vivo Photoacoustic Imaging of Blood Vessels Using an Extreme-Narrow Aperture Sensor", IEEE Journal of Selected Topics in Quantum Electronics, vol. 9, No. 2, pp. 343-346, Mar./Apr. 2003.

R.H. Webb et al., "Scanning Laser Ophthalmoscope," IEEE Transactions on Biomedical Engineering, vol. BME-28, No. 7, pp. 488-492, Jul. 1981.

R.H. Webb, et al., "Confocal Scanning Laser Ophthalmoscope," Applied Optics, vol. 26, No. 8, pp. 1492-1499, Apr. 15, 1987.

R.L. Avery, et al, "Intravitreal Bevacizumab (Avastin) in the Treatment of Proliferative Diabetic Retinopathy", Ophthalmology, vol. 113, No. 10, pp. 1695-1705, Oct. 2006.

S. Fujioka, et al., "Correlation Between Higher Blood Flow Velocity in the Central Retinal Vein than in the Central Retinal Artery and Severity of Nonproliferative Diabetic Retinopathy", Japanese Journal of Ophthalmology, vol. 50, pp. 312-317, 2006.

S. Jiao, et al., "Polarization Effect on the Depth Resolution of Optical Tomography", J. Biomed. Opt., vol. 13, No. 6, JBO Letters 060503-1, 2008.

S. Jiao, et al., "Simultaneous Acquisition of Sectional and Fundus Ophthalmic Images with Spectral-Domain Optical Coherence Tomography," Optics Express, vol. 13, No. 2, pp. 444-452, Jan. 24, 2005.

S. Schmitz-Valckenberg, et al., "Evaluation of Autofluorescence Imaging with the Scanning Laser Ophthalmoscope and the Fundus Camera in Age-related Geographic Atrophy," American Journal of Ophthalmology, vol. 146, pp. 183-192, Aug. 2008.

S. Tang, et al., "Imaging Subcellular Scattering Contrast by Using Combined Optical Coherence and Multiphoton Microscopy", Optics Letters, vol. 32, No. 5, pp. 503-505, Mar. 1, 2007.

S. Wild, et al., "Global Prevalence of Diabetes—Estimates for the Year 2000 and Projections for 2030", Diabetes Care, vol. 27, No. 5, pp. 1047-1053, May 2004.

S. Yazdanfar, et al., "In Vivo Imaging of Human Retinal Flow Dynamics by Color Doppler Optical Coherence Tomography", Archives of Ophthalmology, vol. 121, pp. 235-239, Feb. 2003.

S.A. Boppart, et al., "High-Resolution Optical Coherence Tomography-Guided Laser Ablation of Surgical Tissue", Journal of Surgical Research, vol. 82, pp. 275-284, 1999.

T. Dabbs, et al., "Fiber-Optic Confocal Microscope: FOCON," Applied Optics, vol. 31, No. 16, pp. 3030-3035, Jun. 1, 1992.

T.A. Ciulla, et al., "Diabetic Retinopathy and Diabetic Macular Edema—Pathophysiology, Screening, and Novel Therapies", Diabetes Care, vol. 26, No. 9, pp. 2653-2664, Sep. 2003.

T.S. Kern, et al., "Animal Models of Diabetic Retinopathy", Retinal and Choroidal Angiogenesis, pp. 81-102, 2008.

V.P. Zharov, et al., "In vivo Photoacoustic Flow Cytometry for Monitoring of Circulating Single Cancer Cells and Contrast Agents", Optics Letters, vol. 31, No. 24, pp. 3623-2325, Dec. 15, 2006.

V.V. Yakovlev, et al., "Stimulated Raman Photoacoustic Imaging", Under Review with Proc. Natl. Acad. Sci. USA. (2009).

W. Goebel, et al., "Retinal Thickness in Diabetic Retinopathy - Comparison of Optical Coherence Tomography, the Retinal Thickness Analyzer, and Fundus Photography", Retina, vol. 26, pp. 49-57, 2006.

J.M. Girkin, "Adaptive Optics for Deeper Imaging of Biological Samples", Current Opinion in Biotechnology, vol. 20, pp. 106-110, 2009.

W.R. Freeman, et al., "Simultaneous Indocyanine Green and Fluorescein Angiography Using a Confocal Scanning Laser Ophthalmoscope", Archives of Ophthalmology, vol. 116, pp. 455-463, Apr. 1998.

X. Wang, et al., "Noninvasive Laser-Induced Photoacoustic Tomography for Structural and Functional in vivo Imaging of the Brain", Nature Biotechnology, vol. 21, No. 7, pp. 803-806, Jul. 2003.

Z.Xie, et al., "Laser-Scanning Optical-Resolution Photoacoustic Microscopy," Optics Letters, vo.34, No. 12, pp. 1771-1773, Jun. 15, 2009.

P.N. Marsh, et al., "Practical Implementation of Adaptive Optics in Multiphoton Microscopy" Optics Express, vol. 11, No. 10, pp. 1123-1130, May 19, 2003.

M.J. Booth, et al., "Adaptive Aberration Correction in a Confocal Microscope." Proceedings of the National Academy of Sciences, vol. 99, No. 9, pp. 5788-5792, Apr. 30, 2002.

L. Sherman, et al., "Adaptive Correction of Depth-Induced Aberrations in Multiphoton Scanning Microscopy Using a Deformable Mirror." Journal of Microscopy, vol. 206, pt.1, pp. 65-71, Apr. 2002.

F. Kong, et al. "High-Resolution Photoacoustic Imaging with Focused Laser and Ultrasonic Beams". Applied Physics Letters, vol. 94, 2009.

B. Rao, et al., "Hybrid-Scanning Optical-Resolution Photoacoustic Microscopy for in vivo Vasculature Imaging," Optics Letters, vol. 35, No. 10, pp. 1521-1523, May 15, 2010.

Laser Institute of America, American National Standard for Safe Use of Lasers ANSI Z136.1-2007. Chapter 8. (American National Standards Institute Inc., New York, NY, 2007).

R. Silverman, et al., "Fine-Resolution Photoacoustic Imaging of Eye". Proceedings of SPIE 7564, 2010.

L. Li, et al., "Three-Dimensional Combined Photoacoustic and Optical Coherence Microscopy for in Vivo Microcirculation Studies", Optics Express, vol. 17, No. 19, pp. 16450-16455, Sep. 14, 2009.

O.P.van Bijsterveld, Diabetic Retinopathy. Chapter 13—Histopathology and Pathophysiology of Diabetic Retinopathy (Martin Dunitz 2000).

S. Hu, et al. "Label-Free Photoacoustic Ophthalmic Angiography", Optics Letters, vol. 35, No. 1, pp. 1-3, Jan. 1, 2010.

M. Ruggeri, et al., "Retinal Structure of Birds of Prey Revealed by Ultra-High Resolution Spectral-Domain Optical Coherence Tomography", IOVS Papers in Press, Manuscript iovs.10-5633, Jun. 16, 2010.

S. Prahl, "Optical Absorption of Hemoglobin", SAP, Dec. 15, 1999.

United States Patent Office Action for U.S. Appl. No. 12/726,172 dated Nov. 12, 2010 (14 pages).

* cited by examiner

SYSTEMS AND METHODS FOR PHOTOACOUSTIC OPTHALMOSCOPY

CROSS-REFERENCE TO RELATED APPLICATIONS

This application claims priority benefit of U.S. Provisional Application No. 61/160,907, filed Mar. 17, 2009, and to U.S. Provisional Application No. 61/335,684, filed Jan. 11, 2010, each of which is incorporated herein by reference in their entirety.

FIELD OF THE INVENTION

Various embodiments of the present invention relate to multimodal medical imaging. In particular, various embodiments of the present invention relate to photoacoustic and laser scanning microscopy.

BACKGROUND OF THE INVENTION

Visual loss is often considered the most feared complication of human disease, other than death. Among all the causes that lead to irreversible vision loss, diabetic retinopathy remains a leading cause. Diabetic retinopathy is a vascular disorder that occurs as a complication of diabetes mellitus. It is estimated that more than 10 million adults over the age of 40 in the U.S. have diabetes mellitus. Early detection and treatment of diabetes mellitus could lead to significant societal healthcare savings and prevent the loss of sight for millions of people in the U.S. alone.

Currently, clinical treatment for late stage diabetic retinopathy is associated with unavoidable side effects that include diminished peripheral and night vision as well as loss of vision. As diabetic retinopathy progresses the blood vessels supplying oxygen to the eye become blocked, which leads to decreased oxygen to the retina. Treatment of diabetic retinopathy has increasingly been placed upon detecting progression of the disease at an earlier stage.

SUMMARY

Briefly, in one aspect the invention provides a multimodal imaging system including a laser apparatus for generating a laser beam capable of irradiating a biological sample, an optical coupler operatively connected to the laser for collecting photons reflected from the biological sample and a dual-axis scanner operatively connected to the laser for scanning the laser beam across the biological sample. The system also includes an optical device for delivering the laser beam to the biological sample and an ultrasonic transducer for measuring laser induced ultrasonic waves.

According to another embodiment, the invention provides a method for imaging a biological sample that includes generating a laser beam capable of irradiating the biological sample, the laser beam being generated from a tunable laser system, scanning the laser beam with a dual-axis scanner and collimating and focusing the laser beam on the biological sample with an optical system. Additionally, the method includes irradiating the biological sample based at least in part upon the focused laser beam, collecting reflected photons from the biological sample with an optical coupler and processing the collected photons. Further, the method includes detecting photoacoustic waves in response to the irradiated biological sample, processing the photoacoustic signals and generating an image of the biological sample based at least in part upon the processed photons and photoacoustic signals.

According to another embodiment, the invention includes a fiber optic confocal microscope and a laser scanning optical resolution photoacoustic microscope, the confocal microscope and photoacoustic microscope configured to generate a combined ophthalmic image based at least in part upon a scanned ophthalmic region of interest, photons reflected from the ophthalmic region of interest and photoacoustic waves generated from an irradiated ophthalmic region of interest, wherein the combination uses a single laser light source.

Other aspects of the invention will become apparent by consideration of the detailed description and accompanying drawings.

BRIEF DESCRIPTION OF THE DRAWINGS

FIG. 10a is a side perspective view of a contact lens in combination with a ring transducer in accordance with at least one embodiment of the present invention; and FIG. 10b is a top plan view of the contact lens as shown in FIG. 10a.

DETAILED DESCRIPTION

Figure 1:
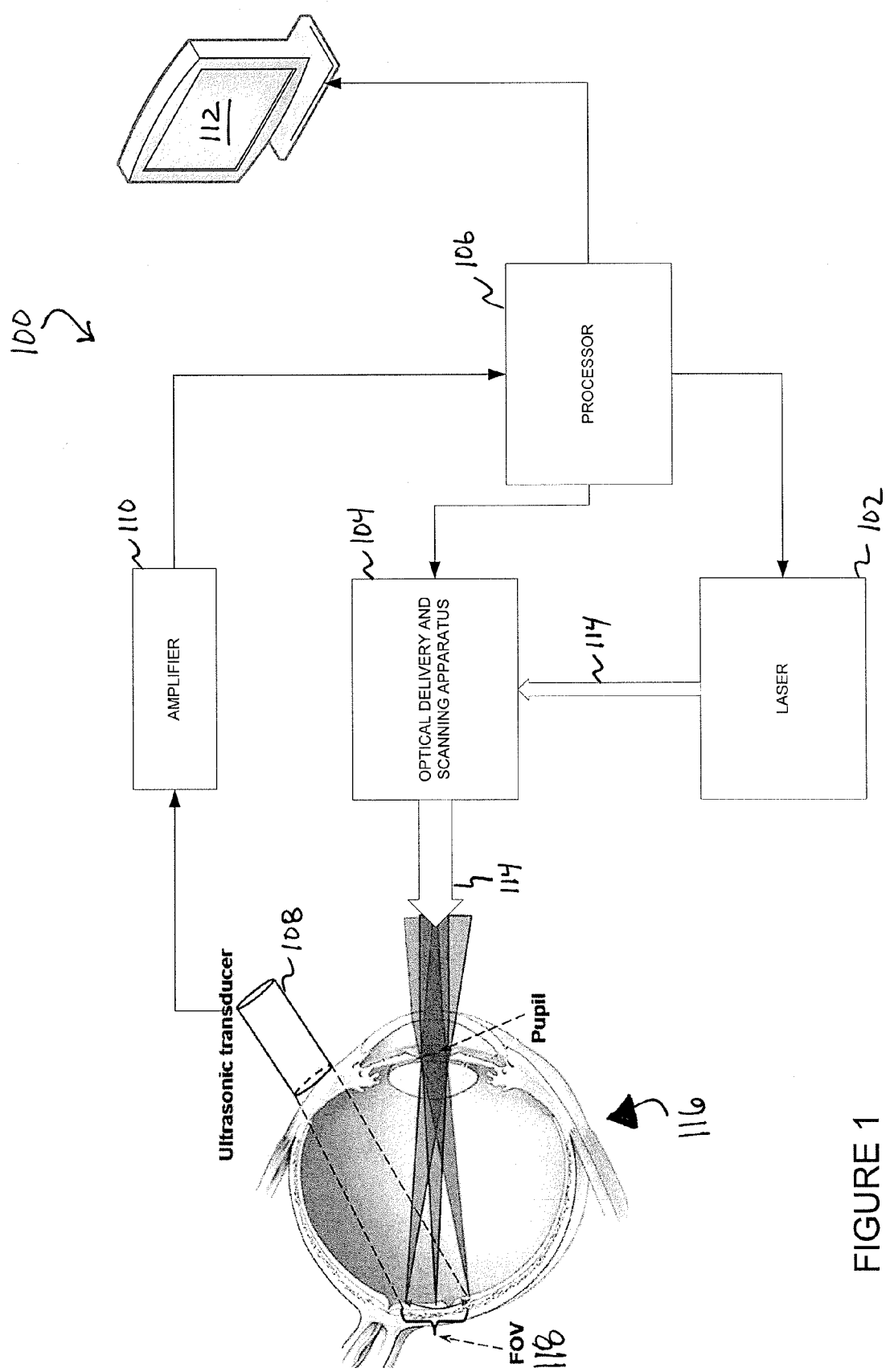
FIG. 1 is a system diagram of an exemplary photoacoustic opthalmoscopy system in accordance with at least one embodiment of the present invention.

Before any embodiments of the invention are explained in detail, it is to be understood that the invention is not limited in its application to the details of construction and the arrangement of components set forth in the following description or illustrated in the following drawings. The invention is capable of other embodiments and of being practiced or of being carried out in various ways. Also, it is to be understood that the phraseology and terminology used herein is for the purpose of description and should not be regarded as limited. The use of "including," "comprising" or "having" and variations thereof herein is meant to encompass the items listed thereafter and equivalents thereof as well as additional items. The terms "mounted," "connected" and "coupled" are used broadly and encompass both direct and indirect mounting, connecting and coupling. Further, "connected" and "coupled" are not restricted to physical or mechanical connections or couplings, and can include electrical connections or couplings, whether direct or indirect. Also, electronic communications and notifications may be performed using any known means including direct connections, wireless connections, etc.

It should be noted that a plurality of hardware and software based devices, as well as a plurality of different structural components may be utilized to implement the invention. Furthermore, and as described in subsequent paragraphs, the specific configurations illustrated in the drawings are intended to exemplify embodiments of the invention and that other alternative configurations are possible. Further, use of the term "processor" is meant to include systems architected in such a way as to have only a single processor or multiple distributed processors functioning serially or in parallel to perform the processing functions. In addition, in multi-processor systems, the description is meant to encompass constructions having all processors in one machine or in one location, or constructions having processors distributed across different machines or locations.

FIG. 1 shows a laser-scanning optical resolution photoacoustic imaging system 100 is provided. The system 100 includes a tunable pulse laser 102, an optical delivery and scanning apparatus 104, a processor 106, an ultrasonic detector 108, an amplifier 110 and graphical user interface (GUI) 112.

The system 100 is a multimodal imaging system that combines photoacoustic microscopy with laser scanning and optical resolution microscopy. A laser beam 114 is delivered to a biological sample 116 by the optical delivery and scanning apparatus 104. The laser beam 114 is a source for irradiating the biological sample 116. Absorbed photons of the irradiated biological sample 116 are detected by the system 100 within high spatial resolution. The system 100 performs a hybrid photoacoustic imaging method that detects the laser-induced ultrasonic waves to acquire distributions of internal optical energy depositions. When laser pulses irradiate biological tissues, optical energy is absorbed by, for example, blood vessels and converted to heat. In many cases, there is a milli-degree temperature rise. The temperature rise is followed by thermoelastic expansions in the tissue of the biological sample 116. These expansions create wideband ultrasonic waves, which are often referred to as photoacoustic waves. The photoacoustic waves are detected and used to quantify the optical absorption properties of the biological sample. Additionally, the photoacoustic waves are used to form an image of the biological sample 116 based upon the optical absorption contrast of the tissue. The resulting image is displayed on the GUI 112.

The biological sample 116 in the present embodiment is a human eye. However, it is contemplated that functional images can be obtained of a multitude of different biological samples 116. By example, the biological sample can include cells and molecules in suspension, physiological appendages, small animal organs, including ears, skin, eyes, brain, and internal organs, and human eyes and skin. In the present embodiment, the laser beam 114 enters through the pupil and is directed to a retinal region of interest, which is identified as the field of view (FOV) 118, within the eye 116. The FOV is also the region being targeted by the ultrasonic transducer 108.

The ultrasonic transducer 108 is kept stationary while information is acquired. Data acquired by the ultrasonic transducer 108 is delivered to the amplifier 110 and then to the processor 106. The processor 106 performs a plurality of functions, and it is contemplated that more than one processor 106 can be employed within the system 100. The processor 106 includes executable code that is capable of performing a variety of functions. In particular, the processor is capable of synchronizing the laser triggering and operation of the optical scanner 132. Some of the various functions performed by the processor 106 include controlling when the laser 102 is triggered and controlling the delivery and scanning apparatus 104, which directly effects how the laser beam 114 is delivered. The processor 106 can be connected to a signal digitizer that stores detected digital signals for image formation.

The processor 116 can be more than one computing device, or a single computing device having more than one microprocessor. It is contemplated that the processor 106 is a stand alone computing system with internal or external memory, a microprocessor and additional standard computing features. The processor 116 can be selected from the group comprising a PC, laptop computer, microprocessor, or alternative computing apparatus or system. The processor 116 receives imaging data that has been obtained through photoacoustic microscopy and laser scanning optical resolution microscopy and generates an image of a biological sample based upon these and other data inputs.

Figure 2:
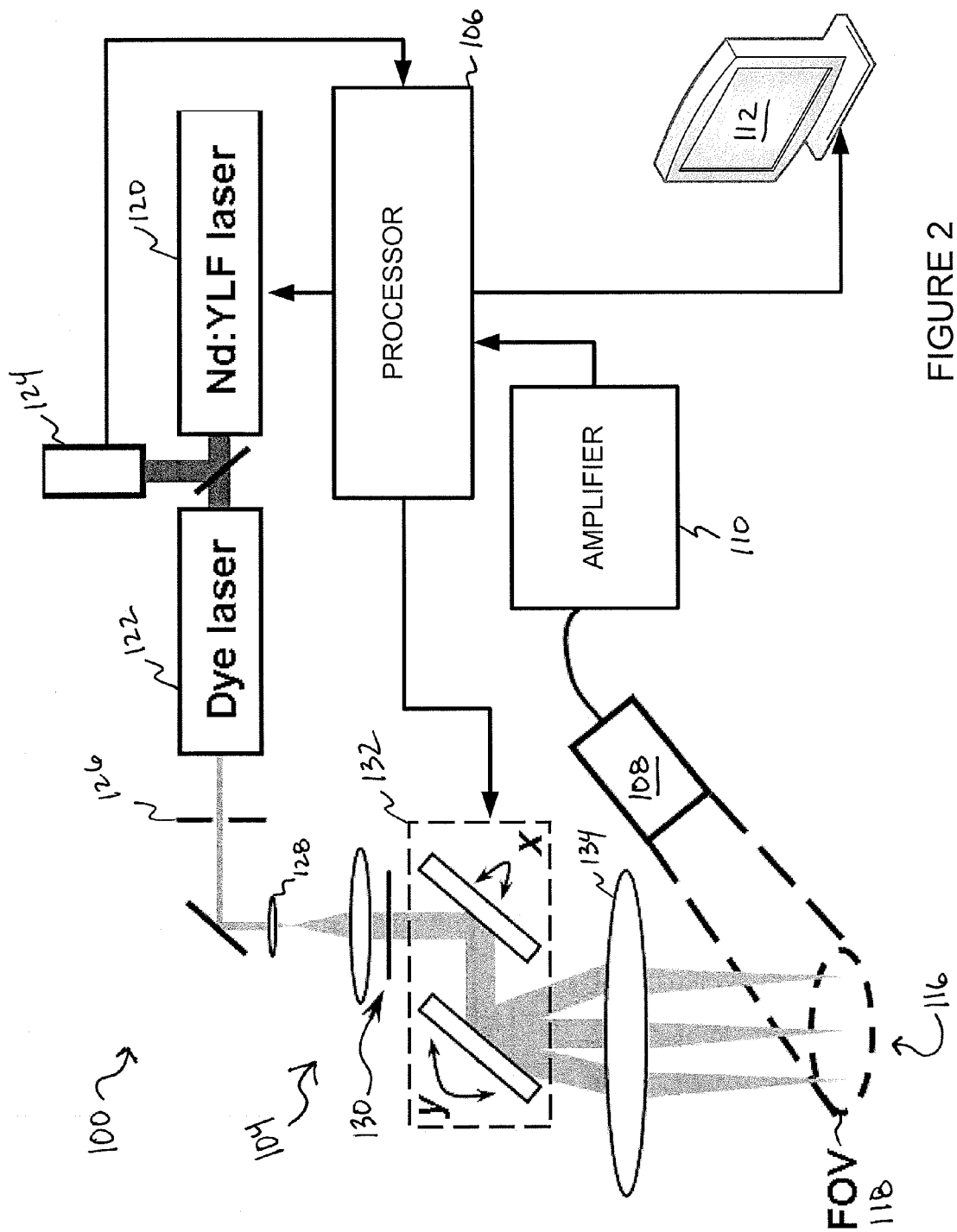
FIG. 2 is a system diagram of another exemplary photoacoustic opthalmoscopy system in accordance with at least one embodiment of the present invention.

FIG. 2 illustrates another embodiment of the laser scanning optical resolution photoacoustic imaging system 100. Like parts are identified using like reference numerals The tunable pulse laser system 102 (See. FIG. 1) includes a neodymium-doped yttrium lithium fluoride (Nd:YLF) laser apparatus 120, a dye laser 122 and a fast photodiode 124. An exemplary laser apparatus 120 includes a model IS8II-E produced by Edge Wave GmbH, Germany and an exemplary dye laser 122 includes a Cobra model produced by Sirah Laser and Plasmatchnik GmbH, Germany.

The dye laser 122 is pumped by the laser apparatus 120 and functions as the irradiation source. The pulse duration of the laser apparatus 120 is about 6 ns. However, it is contemplated that the pulse duration can range from about 1 ns to about 10 ns. Additionally, it is contemplated that the pulse duration can be less than 1 ns and greater than 10 ns. The laser 120 is capable of operating with a pulse repetition rate in a range of about 3 kHz to about 6 kHz. Alternatively, the pulse repetition is less than about 3 kHz and greater than about 6 kHz. The laser 120 is preferably within an optical tuning range of about 500 nm to about 700 nm. Alternatively, the optical tuning range is from about 300 nm to about 1300 nm. It is further contemplated that the tunable pulse laser system 102 is replaced with a plurality of individual fixed wavelength lasers, the wavelengths being within the ranges identified above, that are controlled by the processor 116.

The photodiode 124 relays laser beam 114 information to the processor 106, such as detecting the laser pulses. In addition, the photodiode provides information to the processor 106, which is capable of triggering the acquisition of data to avoid the impact of laser jittering. The energy of each laser pulse is recorded by the photodiode 124 and sent to the processor 106 for storage in a memory storage device (not shown). Compensation for pulse energy instability can be achieved by utilizing energy of each laser pulse. An exemplary fast photodiode includes a model DET10A manufactured by Thorlabs, Newton, N.J.

The optical delivery and scanning system 104 includes an iris 126, a beam expander 128, an attenuator 130, a dual-axis scanner 132 and an objective lens 134. The laser beam 114 is spatially filtered by the iris 126 and expanded by the beam expander 128. (Model BE03M-A, Thorlabs) In the present embodiment, the attenuator 130 is a neutral density filter. (Model FW2AND, Thorlabs) The expanded and attenuated laser beam 114 passes through the dual-axis scanner 132, which is, by example, an x-y galvanometer (Model 6230H, produced by Cambridge Technology Inc., Lexington, Mass. and Model QS-10, Nutfield Technology). After passing through an objective lens 134 the laser beam is focused on a biological sample 116 to be irradiated. Alternatively, the optical scanner 132 can be a polygon mirror scanner or a combination of a dual-axis scanner and a polygon scanner.

In another embodiment, the optical delivery system 104 is based on traditional optics. With traditional optics the laser light beam can be expanded and collimated to cover a biological sample, such as the pupil of an eye, whether the eye is dilated or undilated. The cornea and lens of the eye focus the collimated light on to a retinal region of interest. To compensate for the refractive error of the eye, for example myopia, the position of the objective lens of the optical delivery system 104 is adjustable to ensure adequate focus of the light onto the retinal region of interest. Considering the size of an average human pupil (about 7 mm in diameter) and the aberration of the eye, the expected optical focusing spot is about 10 μm. The lateral resolution of the present embodiment is about 10 μm. Alternatively, the lateral resolution can be adjusted less than about 10 μm and greater than about 10 μm.

In yet another embodiment, the optical delivery system 104 is based upon adaptive optics that includes a wavefront sensor, a deformable mirror and processor (not shown). The light source is either the existing pulse laser beam 114 or an additional laser light coupled to the system 104. Light reflected from the fondus of an eye is partially reflected by the beam splitter into the wavefront sensor, which detects the disturbance of the wavefront sensor caused by the aberrations of the eye and optical delivery system. Based at least in part upon the output of the wavefront sensor the processor computes the compensation and transfers the compensation signal to the deformable mirror. The deformable mirror applies phase modulations to the laser beam to compensate for the disturbance.

Two-dimensional scanning of the optical focus is achieved by a dual-axis galvanometer, which can be performed regardless of the various optical delivery methods discussed herein. The dual-axis optical scanner 132 is capable of various types of scanning, such as two dimensional scanning, raster scanning, spiral scanning and circular scanning According to at least one embodiment of the present invention, the ultrasonic detectors are kept stationary on the eyelids of a human subject while two-dimensional optical scanning is performed. Ultrasound gel is used for better coupling between the detector and the eyelid. Since the ultrasound detectors 108 are kept stationary, the imaging FOV is the ultrasound detection region. The center frequency of the ultrasonic transducer is chosen according to the diameters of the major retinal vessels, which range from about 20 μm to about 100 μm. The frequency ranges from about 10 MHz to about 50 MHz. The bandwidth of the detector 108 is preferably greater than about 60% in order to provide high axial resolution.

The ultrasound detector 108 detects and measures laser induced ultrasonic waves generated by an irradiated biological tissue. The data detected and measured by the ultrasound transducer 108 is transmitted to the processor 106 for ultimately generating an image of the biological sample based at least in part upon the photoacoustic waves, and displayed on the GUI 112. In the present embodiment, the ultrasound transducer 108 has a stationary position with respect to the biological sample 116 and is selected from the group comprising a single stationary detector, an array of detectors, a contact lens integrated with an ultrasound detector and a contact lens integrated with an array of detectors. The transducer 108 is selected to operate in a range of about 10 MHz to about 50 MHz. Alternatively, the transducer operates at less then about 10 MHz or greater than about 50 MHz.

Figure 3:
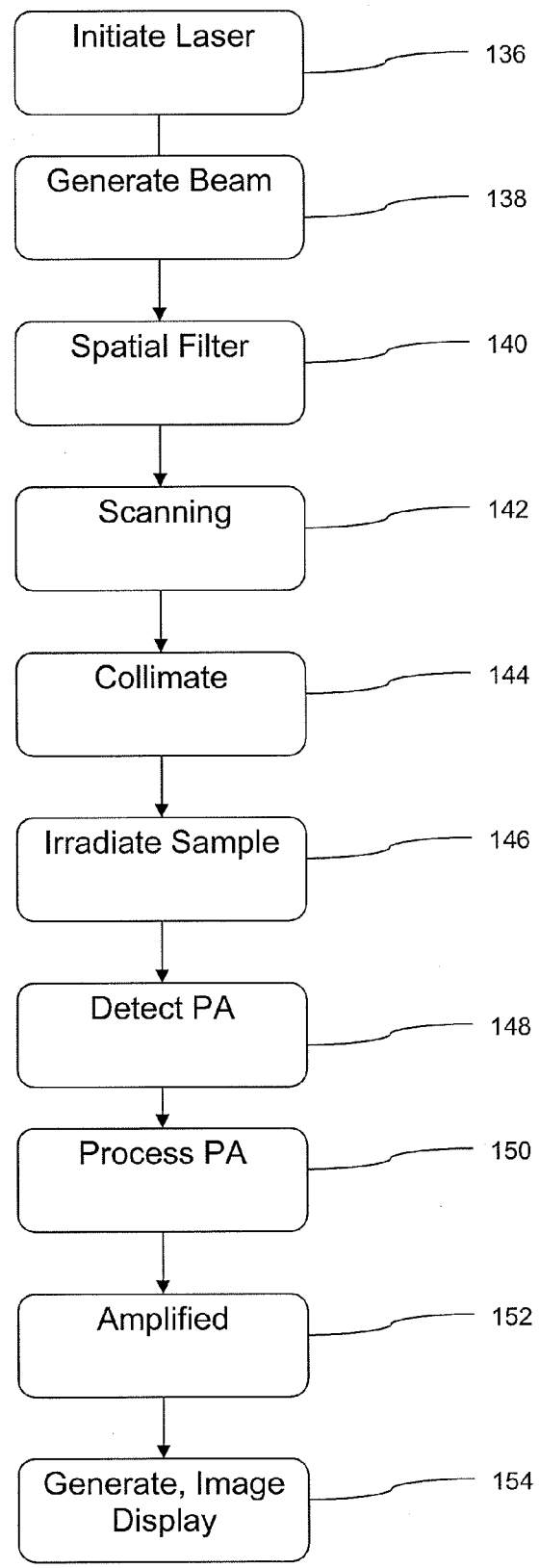
FIG. 3 is a flow chart representing a method for noninvasive ophthalmic imaging in accordance with at least one embodiment of the present invention.

FIG. 3 illustrates an exemplary method of noninvasive ophthalmic imaging. The system 100 (See FIG. 2) is initiated at step 136 and a laser beam is generated from a tunable laser system at step 138. The laser beam is capable of irradiating a biological sample, which in turn generates photoacoustic waves. The laser beam 114 transmitted from a dye laser is spatially filtered by an iris at step 140. This is followed by scanning the laser beam 114 with a dual-axis scanner at step 142, which provides two-dimensional scanning of the laser beam within the field of view for the region of interest on the biological sample. Prior to reaching the biological sample, the laser beam is collimated and focused on the biological sample with an optical apparatus at step 144. The biological sample is irradiated after the focused laser beam is delivered at step 146. In response to the irradiated biological sample, photoacoustic waves are detected at step 148 and processed at step 150. The photoacoustic waves are amplified by a wideband amplifier at step 152, followed by digitizing the photoacoustic signals and storing them within the processor 106. Alternatively, the signals are stored by a data acquisition board operatively connected to the processor 106. Based upon the scanned data and photoacoustic signals the processor generates a functional image of the biological sample and displays the image on the GUI 112 at step 154.

In order to measure functional information such as $sO_2$, photoacoustic (PA) imaging performs multi-wavelength measurements within proper optical spectral ranges. This is in the same way as does NIRS, where HbR and $HbO_2$ are treated as the dominant optical absorbers at each wavelength $(\lambda_i)$. Thus the blood absorption coefficient $\mu_a(\lambda_i)(cm^{-1})$ can be expressed through Equation Set 1.

$$\mu_a(\lambda_i) = \epsilon_{HbR}(\lambda_i)[HbR] + \epsilon_{HbO_2}(\lambda_i)[HbO_2], \quad \text{Equation Set 1}$$

$\epsilon_{HbR}(\lambda_i)$ and $\epsilon_{HbO_2}(\lambda_i)$ are the known molar extinction coefficients $(cm^{-1}M^{-1})$ of HbR and $HbO_2$ at wavelength $\lambda_i$, respectively; and [HbR] and $[HbO_2]$ are the concentrations of the two forms of hemoglobin, respectively. Since the amplitude of the acquired localized PA signal $\Phi(\lambda_i, x, y, z)$ is proportional to the local optical energy deposition, the $\mu_a(\lambda_i)$ can be replaced by $\Phi(\lambda_i, x, y, z)$ to calculate the [HbR] and $[HbO_2]$ in relative values. Least-squares fitting leads to Equation Set 2:

$$\begin{bmatrix} [HbR] \\ [(HbO_2)] \end{bmatrix}_{(x,y,z)} = (M^T M)^{-1} M^T \Phi(x, y, z) K, \quad \text{Equation Set 2}$$

Where $$M = \begin{bmatrix} \varepsilon_{HbR}(\lambda_1) & \varepsilon_{HbO_2}(\lambda_1) \\ \vdots & \vdots \\ \varepsilon_{HbR}(\lambda_n) & \varepsilon_{HbO_2}(\lambda_n) \end{bmatrix},$$

$$\Phi(x, y, z) = \begin{bmatrix} \phi(\lambda_1, x, y, z) \\ \vdots \\ \phi(\lambda_n, x, y, z) \end{bmatrix},$$

K is the proportionality coefficient that is related to the ultrasonic parameters and the wavelength-dependent change of the local optical fluence as light passes through the skin. Thus the $sO_2$ image is calculated using Equation Set 3.

$$sO_{2(x,y,z)} = \frac{[HbO_2]_{(x,y,z)}}{[HbO_2]_{(x,y,z)} + [HbR]_{(x,y,z)}} \quad \text{Equation Set 3}$$

Due to the unknown coefficient K, only relative concentration of the HbR and $HbO_2$ are calculated from Equation Set 2. However, the $sO_2$ from Equation Set 3 is an absolute measurement. Although two wavelengths are enough to determine $SO_2$ in principle, it is recommended to use more wavelengths in order to reduce the influence of measurement error. Published molar extinction coefficients of HbR and $HbO_2$ are used in Equation Set 2.

Various embodiments of the present invention provide a laser scanning optical resolution photoacoustic microscope 100. Higher scanning speed is enabled by the laser scanning systems described above. Higher scanning translates into increased data acquisition over previously known imaging modalities. Additionally, complete raster scanning and other complex scanning patterns such as concentric circular scanning and two dimensional arc scanning are available with the present system 100 that allow localized measurements of single vessels that translates into improved visualization and detection of maladies within the vessels. Experiments relating to various embodiments of the present invention are discussed within the article *Laser-Scanning Optical Resolution Photoacoustic Microscopy*, Optics Letters, Vol. 34, No. 12, hereby incorporated by reference in its entirety herein.

Figure 4:
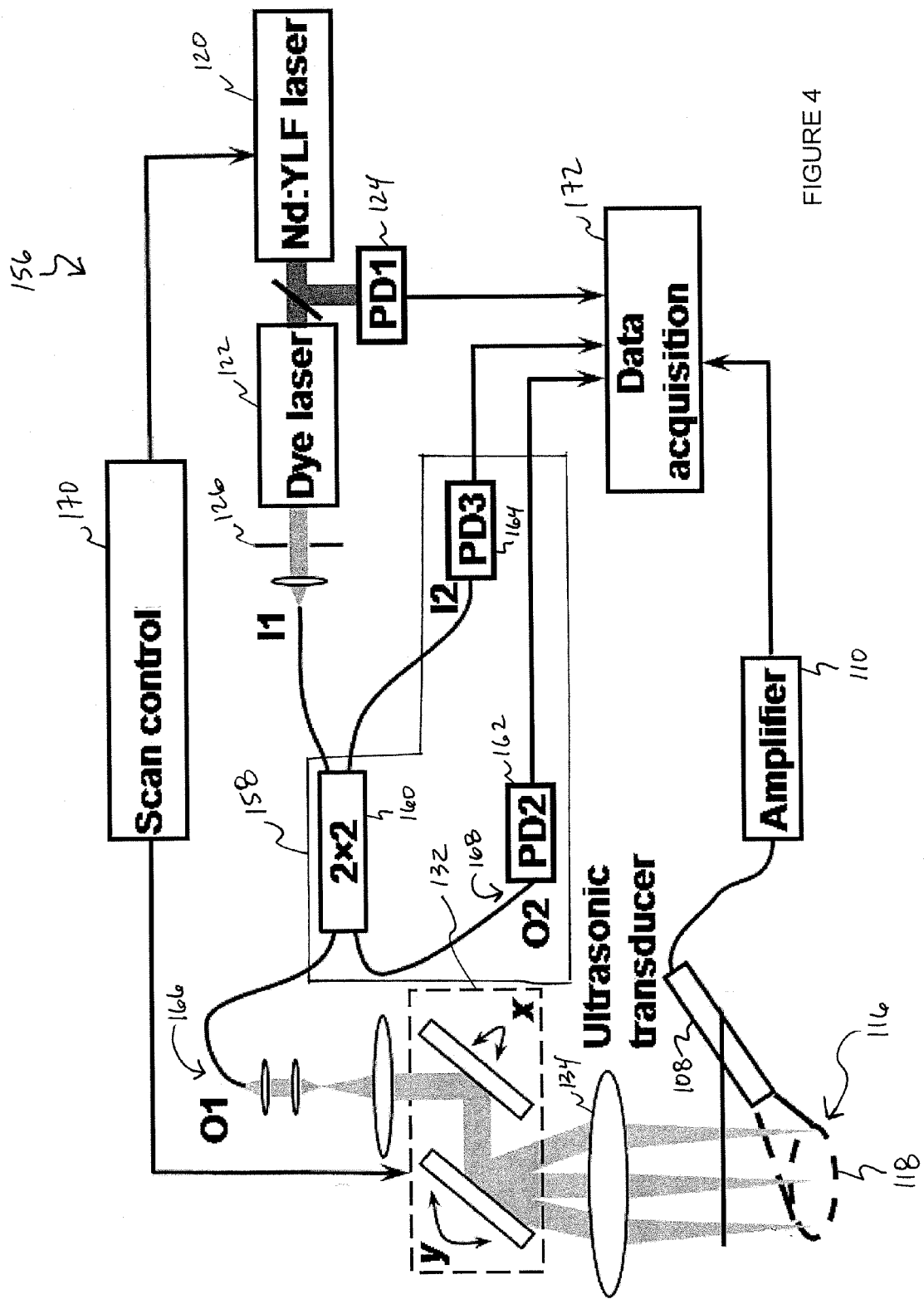
FIG. 4 is a system diagram of an exemplary confocal photoacoustic opthalmoscopy system in accordance with at least one embodiment of the present invention.

FIG. 4 illustrates a confocal scanning laser photoacoustic microscope system 156. The system 156 includes similar elements as the system 100 provided in FIG. 3, but utilizes a confocal scanning laser microscopic apparatus 158. The apparatus 158 includes an optical coupler 160, a second photodiode 162 and a third photodiode 164. The optical coupler 160 includes a first output arm 166 and a second output arm 168. Although a single processor is contemplated, the present embodiment utilizes a scan control processor 170 and a data acquisition processor 172.

The exemplary system 156 generally provided in FIG. 4 can include a variety of exemplary elements. By example, a tunable dye laser 122 pumped by a ND:YLF laser apparatus 120 having a pulse duration of about 6 ns can be used as a biological sample 116 irradiation source. The output wavelength of the irradiation source can vary depending upon system 156 parameters. By example, the wavelength is selected in a range of about 500 nm to about 900 nm. It is contemplated that the wavelength can be less than 500 nm and greater than 700 nm.

The laser beam 114 is transmitted by the dye laser 122 and spatially filtered by an iris 126 and attenuated by a neutral density filter (not shown) before entering a confocal scanning laser microscopic apparatus 158. The apparatus 158 includes a 2×2 single-mode optical fiber coupler 160 (Model FC-632, Thorlabs Inc., Newton, N.J.) operatively connected to the laser 122, a second photodiode 162 and a third photodiode 164. The output light from the optical coupler first arm 166 is collimated and expanded. An exemplary diameter is between about 5 mm and 15 mm. The expanded laser beam is scanned by a dual-axis galvanometer 132. An objective lens 134 is used to focus the laser beam within the region of interest 118 upon the biological sample 116. An exemplary objective lens is an achromatic lens with a focal length of about 40 mm. The second output arm 168 directs output light from the optical coupler 158 to the second photodiode 162 (Model DET10A, Thorlabs Inc., Newton, N.J.). The second photodiode records the energy of every laser pulse generated by the laser 122. This energy data is fed to the processor 172 and used to compensate for energy instability. The detected photoacoustic amplitude is normalized, by example it is divided, by the detected laser pulse energy for the compensation. Furthermore, the amplitude of the photoacoustic signal is proportional to the laser energy.

A confocal image of the biological sample is generated based at least in part upon the laser light photons reflected from the biological sample. The photons are detected by the third photodiode 164 and transmitted to the processor 172. An exemplary third photodiode 164 is a 10 MHz Si photodiode (Model 2107-FC, New Focus Inc., Santa Clara, Calif.). Generation of confocal images from a fiber optic coupler can be generated by several processes previously known. By example, the processor 106 undertakes various calculations and processes to generate an image, such as plotting the detected optical intensity against the spatial location of the optical focus, thereby generating an image. Acquisition of data for the biological sample was triggered by laser pulses directed by the first photodiode 124, which is designed to avoid laser jittering.

In parallel with the confocal image generation an ultrasonic transducer 108 detects induced photoacoustic waves emanating from the biological sample. The photoacoustic waves are amplified by the amplifier 110 and transmitted to the processor 172. The processor 172 generates photoacoustic microscopic images based at least in part upon the photoacoustic waves. The processor 172 merges the photoacoustic and confocal based images to provide a single multimodal functional image of a biological sample.

The exemplary system 156 and the elements identified above represent the combination of a fiber optic confocal microscope and a laser scanning optical resolution photoacoustic microscope. The system 156 is configured to generate a combined ophthalmic image based at least in part upon a scanned ophthalmic region of interest, photons reflected from the ophthalmic region of interest and photoacoustic waves generated from an irradiated ophthalmic region of interest. As shown in FIG. 4, the system 156 uses a single laser light source 122. In another embodiment, it is contemplated that multiple laser light sources can be integrated within the system 156.

The system 156 configuration was designed to permit multimodal ophthalmic imaging, specifically the novel integration of laser scanning optical resolution microscopy and a fiber optic confocal microscopy. In particular, these traditionally divergent technologies were integrated with the use of a single laser light source, thereby allowing simultaneous imaging of a biological sample based at least in part upon optical absorption and scattering contrasts.

The exemplary system 156 is also referred to as a multimodal ophthalmic imaging system. As described above, the system 156 provides a photoacoustic microscope elements for generating functional images of a biological sample. The optical coupler 158, photodiodes 162,164 and processor 172 combine to form a fiber optic confocal microscope for generating functional images of the biological sample. The processor 172 registers the photoacoustic and confocal generated images based at least in part upon a single laser source to provide an enhanced functional image of the biological sample, which can be displayed on a GUI 112.

Figure 5:
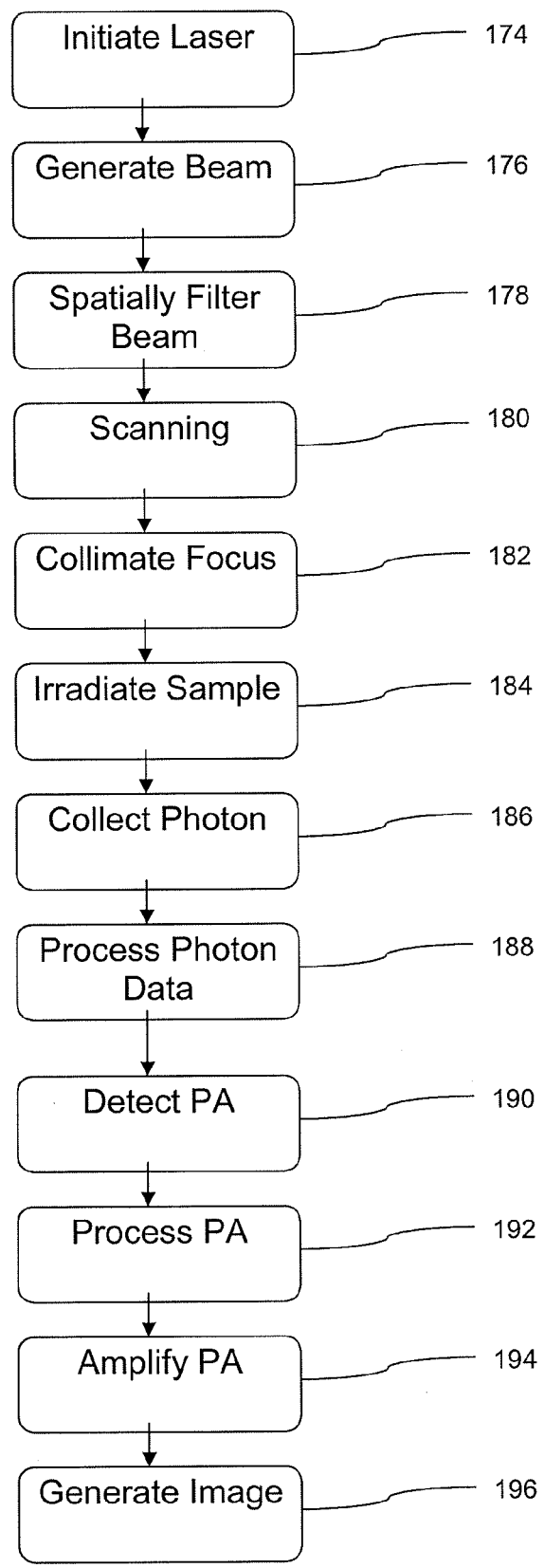
FIG. 5 is a flow chart representing another method for noninvasive ophthalmic imaging in accordance with at least one embodiment of the present invention.

FIG. 5 illustrates an exemplary method of noninvasive ophthalmic imaging using a confocal scanning laser microscope. The system 156 (See FIG. 4) is initiated at step 174 and a laser beam is generated from a tunable laser system at step 176. The laser beam is capable of irradiating a biological sample, which in turn generates photoacoustic waves. The laser beam transmitted from a dye laser is spatially filtered by an iris at step 178, followed by scanning the laser beam with a dual-axis optical scanner at step 180, which causes two dimensional scanning of the laser beam within the field of view for the region of interest on the biological sample. Additional scanning techniques are contemplated, such as raster scanning Prior to reaching the biological sample, the laser beam is collimated and focused on the biological sample with an optical apparatus at step 182. The biological sample is irradiated after the focused laser beam is delivered at step 184. Photons reflected from the biological sample are collected at step 186 and processed at step 188. In response to the irradiated biological sample, photoacoustic waves are detected at step 190 and processed at step 192. The photoacoustic waves are amplified by a wideband amplifier at step 194, followed by digitizing the photoacoustic signals and storing them within the processor 106. Alternatively, the signals are stored by a data acquisition board operatively connected to the processor 106. Based at least upon the processed photons and photoacoustic signals, the processor 172 generates a functional image of the biological sample and displays the image on the GUI 112 at step 196.

The biological sample can be selected from a plurality of different animals and organs. In particular, an exemplary biological sample is an eye to be noninvasively imaged by the present embodiment. In another embodiment, mice ears have been imaged using the system 156 described above and reported within the following articles: *Integrated Photoacoustic Microscopy and Fiber-Optic Confocal Microscopy Using a Single Laser Source*, Proceedings of OSA BIOMED, Miami, Fla. (2010) and Collecting Back-Reflected Photons in Photoacoustic Microscopy, Optics Express 18, 1278-1282 (2010), both of which are hereby incorporated by reference in their entirety herein.

System 156 (See FIG. 4) can also be used to for ophthalmic imaging that includes irradiating a retinal region of interest with a laser beam generated from the tunable laser 122. The retinal region of interest is then scanned using a dual-axis galvanometer capable of two-dimensional raster scanning, which is followed by collecting photons reflected from the retinal region of interest with a 2×2 single-mode fiber optical coupler. The photoacoustic waves generated by the irradiated retinal region are then collected by an ultrasound transducer. The processor 172 controls the collection of the photons, recording of the laser pulses and scanning the laser beam within a single time base. Based at least in part upon the scanned retinal region of interest, photons reflected from the retinal region of interest and recorded photoacoustic waves a functional image of the retina is generated. The present system 156 is capable of combining $O_2$ consumption data, metabolic information and blood flow velocity for purposes of generating functional imaging.

Figure 6:
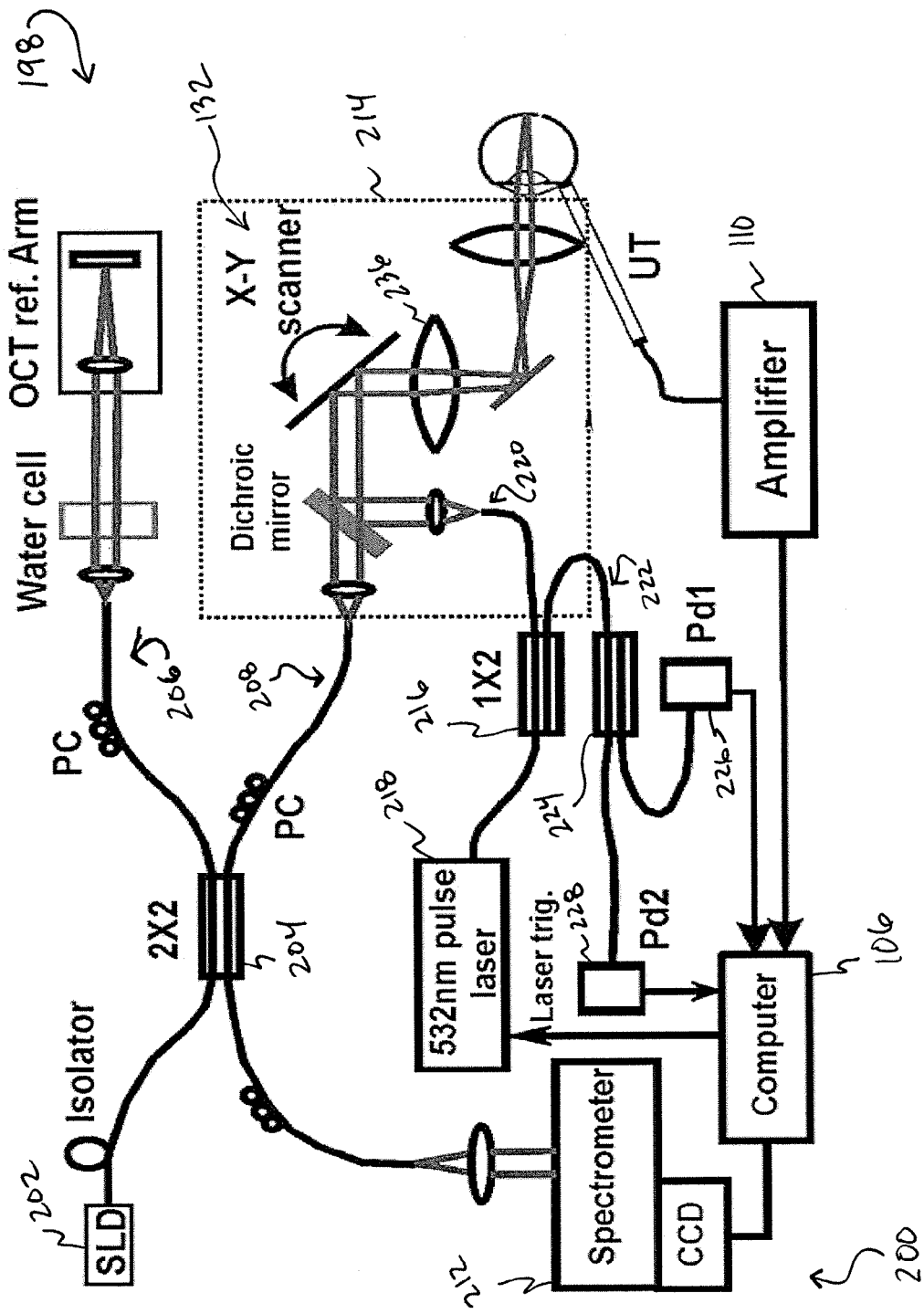
FIG. 6 is an OCT guided photoacoustic opthalmoscopy system in accordance with at least one embodiment of the present invention.

FIG. 6 illustrates an optical coherence tomography (OCT) guided scanning laser optical resolution photoacoustic microscopic system 198. The system 198 utilizes many of the photoacoustic microscopy elements as provided within system 100 (See FIG. 1). The present system 198 incorporates spectral-domain OCT with laser scanning photoacoustic microscopy to provide a method of enhanced imaging of a biological sample 116.

The OCT-guided laser scanning photoacoustic microscope 198 includes a tunable laser 120 capable of irradiating a biological sample 116 with a laser beam, a dual axis galvanometer 132 for raster scanning the laser beam, and a fiber-based spectral-domain optical coherence tomography (OCT) system capable of generating an OCT probing light beam. The OCT system includes a spectrometer 212 for detecting interference signals within a spectral domain. Additionally, an optical delivery system for merging the laser beam and OCT probing light beam and delivering a merged beam to the biological sample is provided. The system 198 also includes an ultrasound transducer integrated within a contact lens for detecting photoacoustic waves generated by the irradiated biological sample 116. A GUI 112 for displaying an image of the biological sample based at least in part upon the photoacoustic waves and spectrometer detected signals is also provided within the system 198.

The imaging system 198 can be used for ophthalmic imaging by irradiating a retinal region of interest with a merged laser beam generated from a tunable laser and an OCT probing light, which. is scanned together using a dual-axis optical scanner capable of two-dimensional raster scanning. The system controls the recording of photoacoustic waves and scanning a retinal region of interest within a single time base. Then, an ophthalmic image is generated based at least in part upon the recording of photoacoustic waves and scanning a retinal region of interest.

The system 198 includes a spectral domain OCT system 200 capable of generating an OCT probing light beam. The system 200 includes a super luminescent diode light source 202, a fiber coupler 204, a reference arm 206, a sample arm 208 coupled to the photoacoustic apparatus 210 and a spectrometer 212 for detecting interference signals within the spectral domain. The system 198 also includes an optical scanning apparatus 214 for scanning both a laser beam and OCT probing light, as well as delivering the combined or merged light to the biological sample 116 (See FIG. 7). Alternatively, OCT systems presently known and suitable for biological sample imaging can be used for integration with the photoacoustic microscope elements of the system 198. Another embodiment is provided in FIG. 8, which discloses a OCT guided laser scanning photoacoustic microscope system 198.

The spectrometer 212 includes a line scan CCD camera that acquires OCT images. By example, a CCD camera can be configured with an exposure time of 36 μs, which can acquire OCT images with a line rate of 24 kHz while having a measured sensitivity greater than about 95 dB. The calibrated depth resolution is about 6 μm in the biological sample and a lateral resolution of about 20 μm. It is contemplated that alternative OCT techniques can be used, for example, time-domain OCT and swept-laser OCT. The OCT systems can also be implemented in free space. Additionally, it is contemplated that varying exposure time, tissue depth resolution and lateral resolutions can be obtained through use of the spectrometer 212 and similar alternatives.

An exemplary system 198 includes a frequency-doubled Q-switched ND:YLG laser 218 (Model SPOT-10-100-532, Elforlight Ltd., UK) having a 532 nm wavelength, 10 μJ/pulse, 2 ns pulse duration and 30 kHz pulse repetition rate is used as an illumination source. The out put laser 218 light is attenuated with a series of neutral density filters (not shown) before being coupled to a 1×2 single mode optical beam splitter 216. The output laser light from a first arm 220 of the splitter 216 is combined with an OCT light beam in the optical scanning apparatus 214. The second arm 222 of the splitter 216 is connected to a multimode fiber beam splitter 224. The two outputs of the splitter 224 are connected to a first photodiode 226 and a second photodiode 228.

Induced photoacoustic waves of the irradiated biological sample 116 are detected by the ultrasound transducer 108. The signals are amplified by the amplifier 110 and transmitted to a processor/computer 106. Processing of the photoacoustic data is performed as discussed within system 100 herein.

The OCT and photoacoustic aspects of the system 198 are synchronized by the processor 170, 172 despite the difference in the achievable imaging speed of the respective aspects. Automatic registration of the OCT and photoacoustic images is obtained by controlling the timing, within a single time base, of the laser triggering, acquisition of the photoacoustic data, dual-axis galvanometer scanning and OCT data acquisition. By example, an analog-output board (Model PD2-AO-16, United Electronic Industries) can be used to trigger data acquisition by the spectrometer 212 (CCD Camera), the laser 218 and dual-axis galvanometer 132. Photoacoustic data acquisition can be triggered by the photodiode 228 in order to avoid laser jittering.

Figure 7:
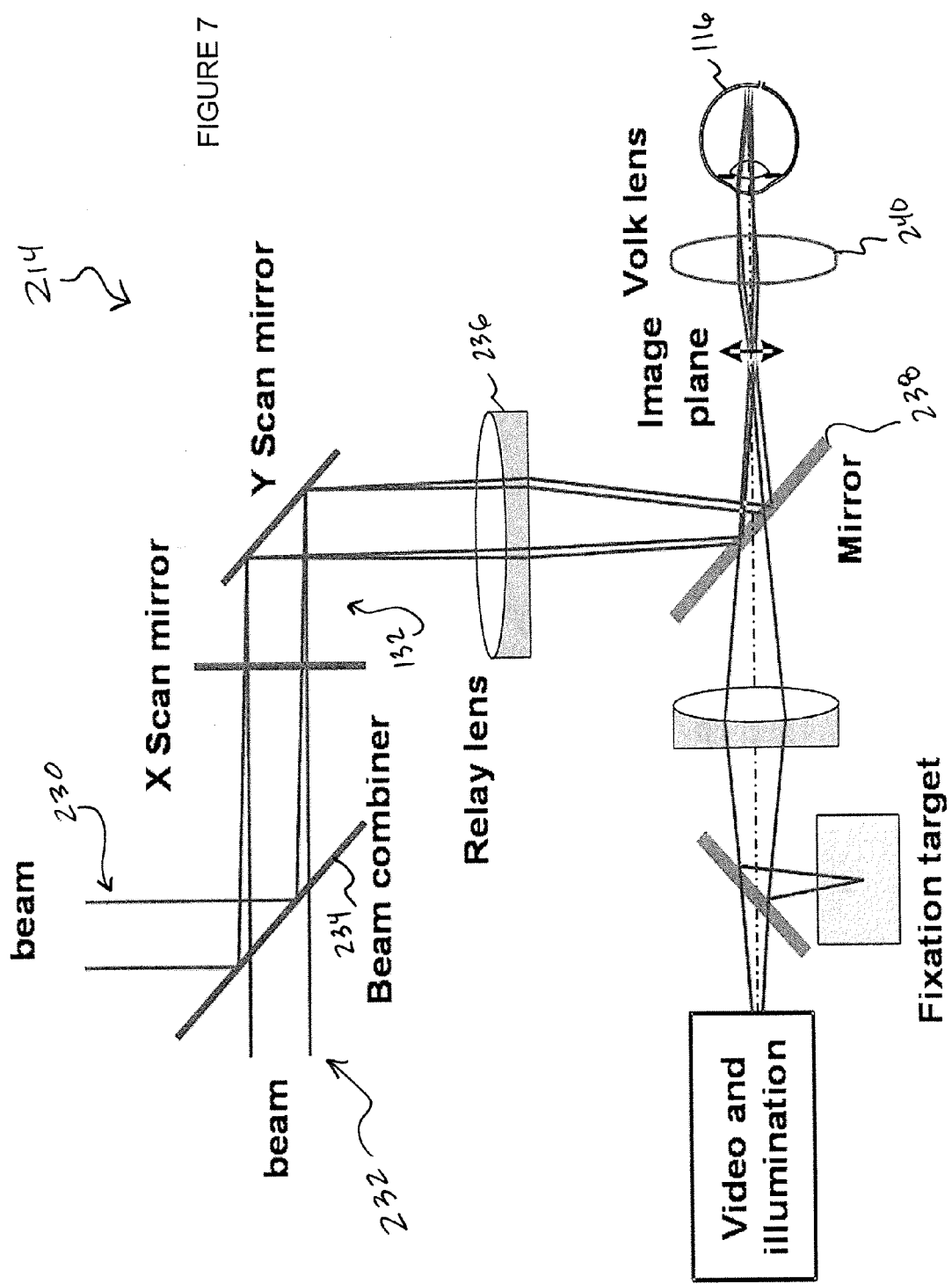
FIG. 7 is a functional flow diagram of an optical delivery and scanning system in accordance with at least one embodiment of the present invention.
Figure 8:
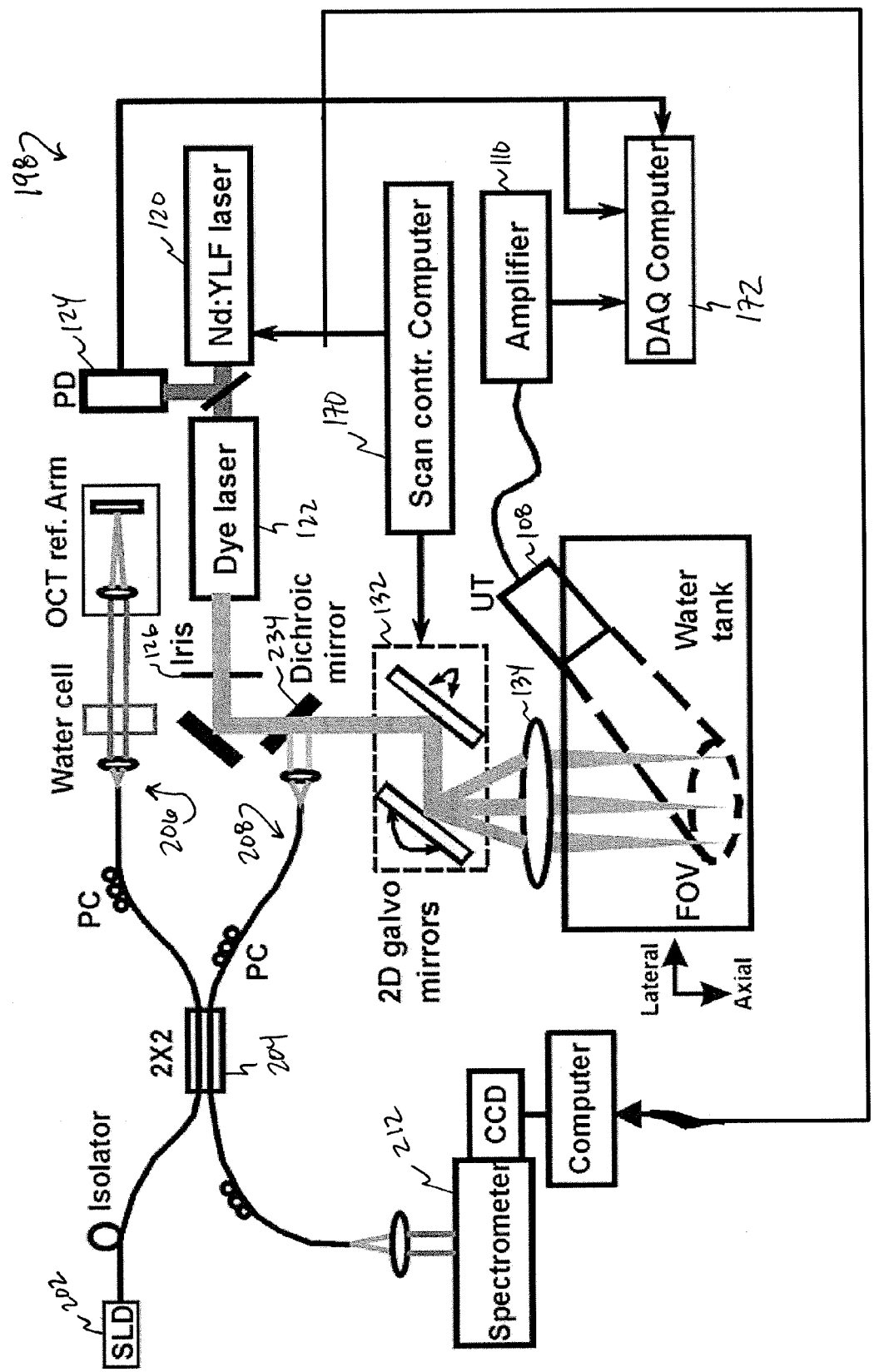
FIG. 8 is another OCT guided photoacoustic opthalmoscopic system in accordance with at least one embodiment of the present invention.

FIG. 7 illustrates a more detailed view of the optical scanning apparatus 214. The apparatus 214 fuses OCT light beams 230 and photoacoustic light beams 232. The light beams are combined with a beam combining dichrotic mirror 234. After combination, the light beams are scanned together with a dual axis scanner 132. The scanner 132 and photoacoustic laser triggering/data acquisition are synchronized as described above. The apparatus 214 further includes a relay lens 236, a mirror 238 and a yolk lens 240.

During image alignment, the laser 218 is turned off and an area of interest is selected through guidance of the OCT image. The OCT image is optimized to ensure good focus of the light upon the retinal region of interest in the eye 116. The system is activated for image acquisition mode once proper alignment of the image is obtained, which includes OCT and photoacoustic based images to be obtained. The same scanning and controlling system 214 is used for obtaining images from the different image modalities.

More than one mode of operation for the combined imaging system 198 is contemplated. By example, a first mode includes a strategy referred to as "imaging mode". The imaging strategy includes the acquisition of both OCT images and photoacoustic based images for an entire image acquisition period. This includes three-dimensional registration of OCT and photoacoustic images. Images for a relatively large area or a single blood vessel are obtained through this imaging mode. This imaging mode allows for two registered three-dimensional images based upon different contrast mechanisms to be acquired simultaneously. Spatial hemoglobin oxygen distribution can be acquired together with flow distribution and vessel morphology. As a result, metabolic rate for any specifically imaged retinal region can be quantified. Photoacoustic images for the present system refer to images obtained through use of laser scanning optical resolution photoacoustic microscopy.

An exemplary second imaging mode is referred to as a "sampling mode", whereby OCT images are obtained for an entire image acquisition period, while photoacoustic images are obtained only when vessels within the biological sample are scanned. The sampling mode provides OCT three-dimensional images and hemoglobin oxygen saturation levels for the vessels based upon the photoacoustic imaging.

The fusion of OCT-based and photoacoustic-based images of the biological sample 116 allows both the anatomical and microvasculature to be visualized in a single volumetric image. The system 198 allows for seamless integration of two images along the lateral directions. In order to register two B-scan images along the axial direction the depth relationship between the photoacoustic and OCT based images must be determined. Then, the photoacoustic volumetric image is shifted along the axial direction to register with the OCT based volumetric image. In another embodiment, mice ears have been imaged using the system 198 described above and reported within the following articles: *Simultaneous Multimodal Imaging with Integrated Photoacoustic Microscopy and Optical Coherence Tomography*, Optics Letters, Vol. 34, No. 19 (2009) and *Naturally Combined Photoacoustic Microscopy and Optical Coherence Tomography for Simultaneous Multimodal Imaging*, Optics Letters, 34, 2961-2963 (2009), both of which are hereby incorporated by reference in their entirety. Additionally, the following article discusses ophthalmic imaging using OCT guided laser scanning photoacoustic microscopy: *Photoacoustic Ophthammoscopy for in vivo Retinal Imaging*, Optics Express, 18, 3967-3972 (2010), which is hereby incorporated by reference in its entirety herein. (All articles referenced and incorporated herein represent the applicant's own work.)

In another embodiment, optical absorption and autofluorescence can be obtained through a modified OCT guided laser scanning optical resolution photoacoustic microscope. A change from the fiber optic based confocal scanning laser opthalmoscope to a free space is made. This modification avoids direct reflection from the fiber tip. Directly reflected light could potentially be stronger than collected fluorescence light. A photomultiplier tube (PMT) or an avalanche photodiode in combination with a dichroic mirror, a band pass filter and a pin-hole are utilized (not shown). The fiber based detection system can be changed to free-space based. An optical filter and a Dichotic mirror will route the fluorescence photons to a pin-hole and then be detected by a high-sensitivity photon detector such as amplified photodiode, photon multiplier tube, and avalanche photodiode. For auto-fluorescence imaging the lateral position is provided by the scanning of the stimulating light. Auto-fluorescence imaging provides information about the distribution and concentration of lipofuscin and melanin, two important pigment components related to the function of RPE.

Figure 9:
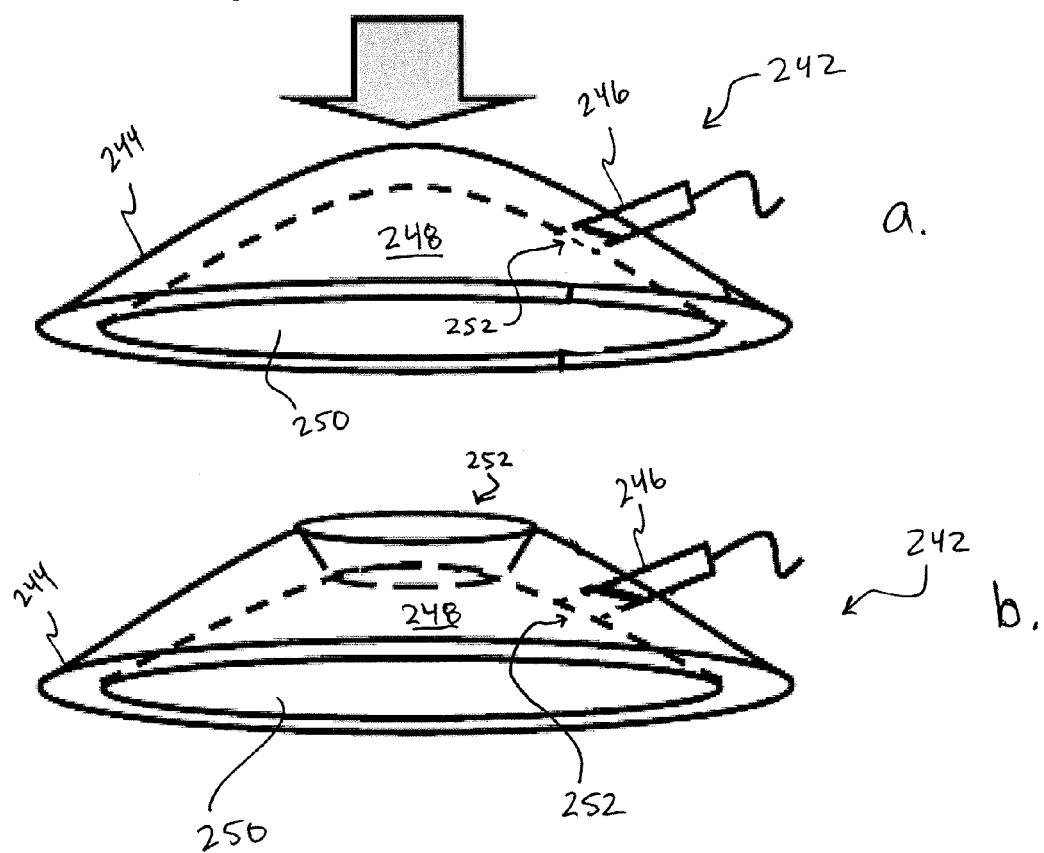
FIG. 9a is a side perspective view of a contact lens in combination with a needle ultrasound transducer in accordance with at least one embodiment of the present invention.
FIG. 9b is a side perspective view of the contact lens according to FIG. 9a, the contact lens having a hollow center.
Figure 10:
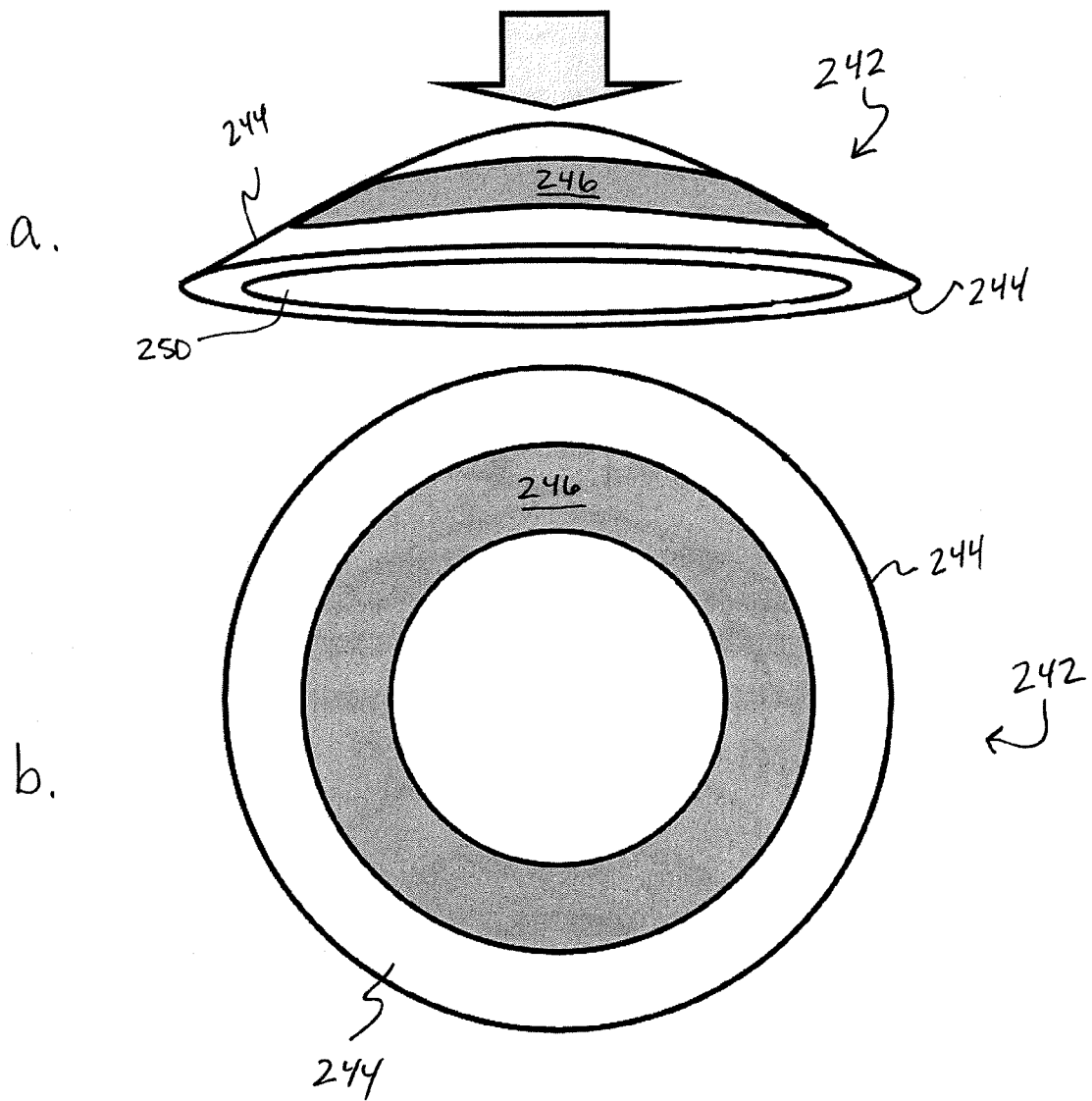

FIGS. 9-10 show an exemplary device 242 including a contact lens 244 combined with an ultrasound transducer 246. The contact lens 244 is configured for placement directly on an eye to be imaged and the ultrasonic transducer 246 is operatively connected to the contact lens 244. The contact lens includes an outer wall 248 to an inner wall 250, the lens having a substantially uniform thickness measured by a distance between the outer wall 248 and inner wall 250. FIG. 9 provides two embodiments of the device 242. In both embodiments the transducer 246 is a needle transducer placed obliquely into the contact lens 244. The first embodiment (FIG. 9a) includes a standard-shaped contact lens. Preferably the contact lens is powerless and has no refractive power. In another embodiment the contact lens is powered and can assist optical focusing within the eye. The contact lens can be configured for an individual's specific ophthalmic physiology. By example, a person with myopia typically requires corrective lens or contact lens in order to have 20/20 vision. A contact lens 244 can be powered based upon the particular myopic structure of an individual's eye. The ultrasound transducer 246 is selected from the group comprising a needle transducer, a ring transducer and an ultrasonic array transducer. It is contemplated that the needle transducer 246 can be positioned in alternative configurations while still obtaining the desired photoacoustic data.

The second embodiment (FIG. 9b) includes the same contact lens as shown in the first embodiment (FIG. 9a) except there is a cut-out at the apex of the contact lens 244, thereby providing a hollow aperture 252 in the contact lens 244. For this embodiment, the contact lens is preferably powerless, as optical illumination reaches the eye directly, unlike the embodiment shown in FIG. 9a. The hollow center aperture 252 is configured and a sized to have a diameter larger than a dilated pupil of the eye upon which the device 242 has been placed. The size of the contact lens 244 is dependent upon the size of the eye, by example, the hollow center 252 has a diameter in a range of about 2 mm to about 8 mm for use in a human eye. It is contemplated that the size of the contact lens 244 and the hollow center 252 can be selected based upon the size of the eye on which the device 242 is placed.

The contact lens 244 can be manufactured from a plurality of suitable materials that are used for conventional contact lenses, including those for refractive correction and fashion. By example, the contact lens material can be selected from the group comprising glass, polymethyl methacrylate, an epoxy composite, materials utilized for hard and soft contact lens, optically transparent and gas permeable materials.

The needle transducer 246 is placed within an orifice that extends from an outer wall 248 to an inner wall 250 of the contact lens 244. After placement of the needle transducer there is a void 252 purposefully configured and located proximal to the inner wall 250. After the device 242 is placed directly onto an eye to be imaged the void will fill with fluid from the eye, such as tears. The natural fluid acts as an ultrasonic coupling medium for enhanced ultrasonic wave detection. Optical illumination passes through the contact lens before entering the eye. The needle transducer can be selected from a variety of commercially available transducers. By example, the needle transducer can have an outer diameter between about 0.5 mm and 1.3 mm, constructed from a PMN-PT single crystal and be housed within a polyamide tube. Exemplary transducers generate a center frequency in a range of about 10 MHz to about 50 MHz. Alternatively, the center frequency can be less than about 10 MHz and greater than about 50 MHz.

It is contemplated that the device 242 has multiple contact lens 244 and transducer 246 configurations. FIGS. 10a and 10b provide two views of an alternative device 242 configuration. A side perspective view is provided in FIG. 10a, and a top plan view of the device 242 is provided in FIG. 10b. A ring shaped ultrasound transducer is combined with a powerless contact lens with a hollow center spatially configured for circumferentially positioning with respect to an iris. The device 242 also has an ultrasound transducer integral to the contact lens and circumferentially positioned with respect to the hollow center of the contact lens 244. The ring transducer 244 is capable of a larger detecting region than the needle configuration. Additionally, the ring transducer 244 is capable of spherical focusing. By example, the ring transducer can be manufactured from a LiNbO3 single crystal, a composite material, PZT and PVDF.

The ring transducer 244 is integral with respect to the contact lens 244. It is contemplated that the ring transducer and contact lens can be combined in a variety of physical configurations. The ring transducer 244 can be attached to the outer wall 248, attached to the inner wall 250, integrated within and completely encompassed by the contact lens, as well as recessed within the contact lens with respect to either the outer wall 248 or inner wall 250. By example, the ring transducer is recessed and attached to the inner wall 250 of the contact lens 244. When the contact lens 244 is placed upon the eye the transducer does not directly touch the eye since it is recessed within the inner wall 250. Similar to the void identified within FIG. 10 a and b, the recess fills with fluid in the eye, such as tears, and acts as a natural ultrasonic coupling medium. It is further contemplated that alternative configuration be selected based upon the distance from the retinal region of interest, the size and shape of the eye, and the specific configurations of the transducer selected.

Insulated wires will be used to connect the transducer with an amplifier outside the contact lens. The amplifier is operatively connected to a digitizer and computer for processing the ultrasonic data. Alternatively, the transmitter can be integrated in the contact lens and the detected acoustic signal can be transmitted wirelessly.

In another embodiment, the device 242 includes a contact lens and ring transducer as shown in FIG. 10a. The device further includes a microprocessor, memory storage device and wireless transmitter (not shown). The device is placed upon an eye and measures photoacoustic waves generated from an irradiated retinal region of interest. The microprocessor digitizes and stores the data within the integrated memory storage device. After the device 242 is no longer acquiring photoacoustic data the device is removed from the eye and placed within close proximity to a wireless receiver for downloading the photoacoustic data acquired by the device. Alternatively, the wireless transmitter is of sufficient power to transmit the data in real-time to a wireless receiver for processing the photoacoustic data and generating functional information and images for the retinal region of interest. It is further contemplated that the wireless transmitter is by default nonfunctional while the device 242 is placed upon the eye in order to prevent the transmission from interfering with data acquisition and health/safety concerns.

According to at least one embodiment, the device 242 acquires photoacoustic waves generated by an irradiated retina. The photoacoustic waves are amplified and digitized for processing by a computer or suitable processor that is capable of generating functional ophthalmic images based at least in part upon the processed photoacoustic waves.

In another embodiment, the transducer is manufactured from a PMN-33% PT/epoxy composite material, which is identified to function within a piezoelectric longitudinal mode. In yet another embodiment, reactive ion etching is utilized to provide crystal post aspect rations and narrow kerfs often needed for high frequency composites with minimal breakage.

It is contemplated that the various systems, methods and embodiments described herein can be used for the diagnosis and evaluation of age-related macular degeneration, geography atrophy, diabetic retinopathy, premature retinopathy, glaucoma, ocular tumors, retinal edema, retinal detachment, several types of ischemic retinopathy, brain disorders and Alzheimer's disease.

Before any embodiments of the invention are explained in detail, it is to be understood that the invention is not limited in its application to the details of construction and the arrangement of components set forth in the following description or illustrated in the following drawings. The invention is capable of other embodiments and of being practiced or of being carried out in various ways.

The invention claimed is:

1. A multimodal imaging system comprising:
    a laser apparatus for generating a laser beam capable of irradiating a biological sample;
    an optical coupler operatively connected to the laser for collecting photons reflected from the biological sample, wherein the optical coupler is selected from the group consisting of a 2×2 single mode optical coupler and a free-space based beam splitter having a pinhole;
    a dual-axis scanner operatively connected to the laser for scanning the laser beam across the biological sample;
    an optical device for delivering the laser beam to the biological sample; and
    an ultrasonic transducer for measuring laser induced ultrasonic waves.

2. The system according to claim 1, wherein the laser apparatus includes a tunable dye laser.

3. The system according to claim 2, wherein the laser beam is spatially filtered.

4. The system according to claim 2, and further comprising a neutral density filter for attenuating the laser beam.

5. The system according to claim 1, and further comprising a first photodiode for detecting laser pulses directly from the laser source.

6. The system according to claim 5, and further comprising a processor for synchronizing laser triggering and optical scanning.

7. The system according to claim 6, and further comprising a second photodiode for detecting laser beams from the optical coupler.

8. The system according to claim 7, wherein the processor compensates for energy instability based at least in part upon the energy of each laser pulse detected by the second photodiode.

9. The system according to claim 8, and further comprising a third photodiode capable of detecting reflected photons and fluorescent photons from the biological sample.

10. The system according to claim 9, wherein the processor generates a confocal-based image of the biological sample based at least in part upon the light detected by the third photodiode.

11. The system according to claim 10, and further comprising a GUI for displaying a functional image of the biological sample based at least upon optical an optical absorption contrast and optical scattering contrast of the biological sample.

12. The system according to claim 11, wherein the functional image is based at least in part upon the ultrasonic waves.

13. The system according to claim 1, wherein the dual-axis scanner is an x-y optical or mechanical scanner.

14. The system according to claim 1, wherein the optical system is capable of producing an optical tuning range from about 300 nm to about 1300 nm.

15. The system according to claim 1, and further comprising a processor for generating an image based at least in part upon an optical absorption contrast and optical scattering contrast of the biological sample.

16. The system according to claim 15, wherein the biological sample is selected from the group consisting of an eye, molecules in suspension and physiological appendages.

17. The system according to claim 15, wherein the ultrasonic detector is selected from the group consisting of a single stationary detector, an array of detectors, and a contact lens integrated with an ultrasonic detector.

18. The system according to claim 17, and further comprising a GUI for displaying a functional retinal image based at least in part upon photoacoustic waves detected by the ultrasonic detector.

19. A method for imaging a biological sample comprising:
generating a laser beam capable of irradiating the biological sample, the laser beam being generated from a tunable laser system;
scanning the laser beam with a dual-axis scanner;
collimating and focusing the laser beam on the biological sample with an optical system;
irradiating the biological sample based at least in part upon the focused laser beam;
collecting reflected photons from the biological sample with an optical coupler, wherein the optical coupler is selected from the group consisting of a 2×2 single mode optical coupler and a free-space based beam splitter having a pinhole;
processing the collected photons;
detecting photoacoustic waves in response to the irradiated biological sample;
processing the photoacoustic signals; and
generating an image of the biological sample based at least in part upon the processed photons and photoacoustic signals.

20. The method according to claim 19, wherein the biological sample is an eye.

21. The method according to claim 20, wherein the image is a functional image of a human retina.

22. The method according to claim 21, wherein the image is obtained noninvasively.

23. The method according to claim 22, wherein the image includes retinal vessel morphology.

24. The method according to claim 21, and further comprising placing a contact lens integrated with a ring transducer directly on an eye to be imaged, the ring transducer configured to detect the photoacoustic signals.

25. The method according to claim 19, and further comprising measuring the selective absorption of incident photons by hemoglobin and generating an $sO_2$ level in retinal vessels.

26. The method according to claim 25, and further comprising generating an HbR value based at least in part upon processing the photoacoustic signals.

27. The method according to claim 19, and further comprising generating an $HbO_2$ value based at least in part upon processing the photoacoustic signals.

28. A method of ophthalmic imaging comprising:
irradiating a retinal region of interest with a laser beam generated from a tunable laser;
scanning the retinal region of interest using a dual-axis galvanometer capable of two-dimensional raster scanning;
collecting photons reflected from the retinal region of interest with a 2×2 single-mode fiber optical coupler;
recording photoacoustic waves generated by the irradiated retinal region;
controlling the collecting, recording and scanning within a single time base; and
generating an ophthalmic image based at least in part upon the scanned retinal region of interest, photons reflected from the retinal region of interest and recorded photoacoustic waves.

29. In combination, a fiber optic confocal microscope and a laser scanning optical resolution photoacoustic microscope, the confocal microscope and photoacoustic microscope configured to generate a combined ophthalmic image based at least in part upon a scanned ophthalmic region of interest, photons reflected from the ophthalmic region of interest and photoacoustic waves generated from an irradiated ophthalmic region of interest, the combination using a single laser light source.

30. The system according to claim 29, and further comprising a GUI for displaying a functional image of an eye based at least in part upon an optical absorption contrast, optical scattering, autofluorescence of the eye and fluorescent signals generated from contrast agents of an the eye.

31. A multimodal ophthalmic imaging system comprising:
a photoacoustic microscope for generating functional images of an eye;
a fiber optic confocal microscope for generating functional images of the eye; and
a processor for registering the photoacoustic and confocal generated images based at least in part upon a single laser source.

* * * * *